United States Patent
Adams et al.

(10) Patent No.: US 11,179,515 B2
(45) Date of Patent: Nov. 23, 2021

(54) PUMP STARTUP ALGORITHMS AND RELATED SYSTEMS AND METHODS

(71) Applicant: Smiths Medical ASD, Inc., Plymouth, MN (US)

(72) Inventors: Grant Adams, Coon Rapids, MN (US); William Rossi, Vadnais Heights, MN (US); Jim Drost, Woodbury, MN (US); Eric Wilkowske, North Oaks, MN (US); Larry Zalesky, Shoreview, MN (US); Taylor Dowden, Terre Haute, IN (US); Jacob Wander, New Brighton, MN (US); Beth Kregel, Minneapolis, MN (US); Sean Riley, Minneapolis, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 137 days.

(21) Appl. No.: 16/388,388

(22) Filed: Apr. 18, 2019

(65) Prior Publication Data

US 2019/0240397 A1    Aug. 8, 2019

Related U.S. Application Data

(63) Continuation of application No. 15/114,475, filed as application No. PCT/JP2015/013049 on Jan. 27, 2015, now Pat. No. 10,293,103.

(Continued)

(51) Int. Cl.
*A61M 5/145* (2006.01)
*A61M 5/142* (2006.01)
(Continued)

(52) U.S. Cl.
CPC .......... *A61M 5/1452* (2013.01); *A61M 5/142* (2013.01); *F04B 17/03* (2013.01);
(Continued)

(58) Field of Classification Search
CPC ................ A61M 5/1452; A61M 5/142; A61M 2205/50; A61M 2205/52;
(Continued)

(56) References Cited

U.S. PATENT DOCUMENTS 3,985,467 A    10/1976    Lefferson
4,037,598 A     7/1977    Georgi
(Continued)

FOREIGN PATENT DOCUMENTS

EP    0 319 267 A2    6/1989
EP    1349596 A1    10/2003
WO    WO 2013/177379 A1    11/2013

OTHER PUBLICATIONS

International Preliminary Report on Patentability, International Application No. PCT/US2015/031049, dated Aug. 25, 2016, 10 pages.

(Continued)

*Primary Examiner* — Lauren P Farrar
(74) *Attorney, Agent, or Firm* — Patterson Thuente Pedersen, P.A.

(57) ABSTRACT

An infusion pump includes a pumping mechanism having at least one sensor and a pump motor and a pump control subsystem configured to control operation of the pumping mechanism, the pump control subsystem including a processor, a memory, and a startup module configured to drive the pump motor at a first rate, receive input from the at least one sensor, and drive the pump motor at a second rate based on the input received from the at least one sensor. Startup algorithms command an infusion pump to reach a targeted delivery rate or steady state in minimal time without requir- (Continued)

ing priming of the pump line or otherwise engaging in known methods of pump startup analysis.

9 Claims, 17 Drawing Sheets

Related U.S. Application Data

(60) Provisional application No. 61/938,264, filed on Feb. 11, 2014.

(51) Int. Cl.
| | | |
|---|---|---|
| *F04B 17/03* | (2006.01) | |
| *F04B 49/02* | (2006.01) | |
| *F04B 49/06* | (2006.01) | |
| *G16H 40/63* | (2018.01) | |
| *F04B 19/22* | (2006.01) | |

(52) U.S. Cl.
CPC .............. *F04B 19/22* (2013.01); *F04B 49/02* (2013.01); *F04B 49/065* (2013.01); *G16H 40/63* (2018.01); *A61M 2005/14208* (2013.01); *A61M 2205/332* (2013.01); *A61M 2205/3334* (2013.01); *A61M 2205/50* (2013.01); *A61M 2205/52* (2013.01)

(58) Field of Classification Search
CPC .. A61M 2005/14208; A61M 2205/332; A61M 2205/3334; G16H 40/63; F04B 19/22; F04B 17/03; F04B 49/02; F04B 49/065
See application file for complete search history.

(56) References Cited

U.S. PATENT DOCUMENTS

| | | | |
|---|---|---|---|
| 4,080,966 | A | 3/1978 | McNally et al. |
| 4,137,913 | A | 2/1979 | Georgi |
| 4,207,031 | A | 6/1980 | Maskrey et al. |
| 4,422,942 | A | 12/1983 | Allington |
| 4,444,546 | A | 4/1984 | Fazemenas |
| 4,525,163 | A | 6/1985 | Slavik et al. |
| 4,686,439 | A | 8/1987 | Cunningham et al. |
| 4,718,576 | A | 1/1988 | Tamura et al. |
| 4,769,153 | A | 9/1988 | Allington |
| 4,772,388 | A | 9/1988 | Allington |
| 4,775,481 | A | 10/1988 | Allington |
| 4,781,824 | A | 11/1988 | Allington |
| 4,833,384 | A | 5/1989 | Munro et al. |
| 4,882,781 | A | 11/1989 | Allington |
| 4,898,578 | A | 2/1990 | Rubalcaba, Jr. |
| 5,040,126 | A | 8/1991 | Allington |
| 5,713,856 | A | 2/1998 | Eggers et al. |
| 6,368,314 | B1 | 4/2002 | Kipfer et al. |
| 6,394,771 | B2 | 5/2002 | Butterfield |
| 6,416,291 | B1 | 7/2002 | Butterfield et al. |
| 7,029,456 | B2 | 4/2006 | Ware et al. |
| 7,734,323 | B2 | 6/2010 | Blomquist |
| 7,751,907 | B2 | 7/2010 | Blomquist |
| 7,758,547 | B2 | 7/2010 | Tonelli et al. |
| 8,182,445 | B2 | 5/2012 | Moubayed et al. |
| 8,208,984 | B2 | 6/2012 | Blomquist |
| 8,219,222 | B2 | 7/2012 | Blomquist |
| 8,221,345 | B2 | 7/2012 | Blomquist |
| 8,231,578 | B2 | 7/2012 | Fathallah et al. |
| 8,234,128 | B2 | 7/2012 | Martucci et al. |
| 8,291,337 | B2 | 10/2012 | Gannin et al. |
| 8,417,545 | B2 | 4/2013 | Galasso et al. |
| 8,444,394 | B2 | 5/2013 | Koehl |
| 8,882,701 | B2 | 11/2014 | DeBelser |
| 1,029,310 | A1 | 5/2019 | Adams et al. |
| 2005/0143864 | A1 | 6/2005 | Blomquist |
| 2006/0064053 | A1* | 3/2006 | Bollish .............. A61M 5/16895 604/31 |
| 2008/0171967 | A1 | 7/2008 | Blomquist |
| 2008/0172029 | A1 | 7/2008 | Blomquist |
| 2008/0172031 | A1 | 7/2008 | Blomquist |
| 2008/0255517 | A1 | 10/2008 | Nair |
| 2008/0288115 | A1 | 11/2008 | Rusnak et al. |
| 2009/0131859 | A1 | 5/2009 | DelCastillo et al. |
| 2009/0157003 | A1 | 6/2009 | Jones et al. |
| 2011/0137239 | A1 | 6/2011 | DeBelser et al. |
| 2011/0152830 | A1 | 6/2011 | Ruchti et al. |
| 2011/0208155 | A1 | 8/2011 | Palerm et al. |
| 2012/0138272 | A1 | 6/2012 | Zimmerman et al. |
| 2012/0203195 | A1 | 8/2012 | Pope et al. |
| 2012/0215199 | A1 | 8/2012 | Moberg et al. |
| 2012/0226124 | A1 | 9/2012 | Blomquist |
| 2012/0226259 | A1 | 9/2012 | Yodfat et al. |
| 2012/0232484 | A1 | 9/2012 | Blomquist |
| 2012/0232485 | A1 | 9/2012 | Blomquist |
| 2012/0232521 | A1 | 9/2012 | Blomquist |
| 2012/0265722 | A1 | 10/2012 | Blomquist |
| 2013/0046281 | A1 | 2/2013 | Javitt |
| 2013/0317324 | A1 | 11/2013 | Yodfat et al. |
| 2014/0188076 | A1* | 7/2014 | Kamen .............. A61M 5/16831 604/506 |
| 2016/0346462 | A1 | 12/2016 | Adams et al. |

OTHER PUBLICATIONS

Office Action dated Dec. 14, 2018 for Chinese Application No. 201580006498.5, 7 pages.
Search Report dated Feb. 13, 2018 for EP Application No. 15749149.9, 17 pages.
"Infusion pump algorithm accelerates initial drug delivery", Feb. 2, 2017, 2 pages.
Communication dated Oct. 4, 2017 for EP Application No. 15749149.9, 15 pages.
International Search Report for corresponding International App No. PCT/US2015/013049 dated Jun. 12, 2015; 4 pages.
Written Opinion for corresponding International App No. PCT/US2015/013049 dated Jun. 12, 2015; 8 pages.
Flygt, "Start of pump systems, Analysis and calculations," http://www.xylemwatersolutions.com/scs/russia/Documents/3329245.pdf Accessed on May 29, 2013; 10 pages.
Application and File history for U.S. Appl. No. 15/114,475, filed Jul. 27, 2016. Inventors: Adams et al.
Office Action dated Jan. 27, 2021 for EP Application No. 15749149.9, 6 pages.

\* cited by examiner

PUMP STARTUP ALGORITHMS AND RELATED SYSTEMS AND METHODS

RELATED APPLICATIONS

This application is a continuation of application Ser. No. 15/114,475 filed Jul. 27, 2016, which is a National Phase entry of PCT Application No. PCT/US2015/013049 filed Jan. 27, 2015, which claims the benefit of U.S. Provisional Application No. 61/938,264 filed Feb. 11, 2014, which is incorporated herein by reference in its entirety.

TECHNICAL FIELD

Subject matter hereof relates generally to infusion pumps, and more particularly, to startup algorithms and related systems and methods for infusion pumps.

BACKGROUND

Infusion pumps are extremely useful medical devices for providing prescribed fluids, drugs, and other therapies to patients. For example, medications such as antibiotics, chemotherapy drugs, and pain relievers are commonly delivered to patients via an infusion pump, as are nutrients and other supplements. Infusion pumps have been used in hospitals, nursing homes, and in other short-term and long-term medical facilities, as well as for in-home care. Infusion pumps can be particularly useful for the delivery of medical therapies requiring an extended period of time for their administration. There are many types of infusion pumps, including large volume, patient-controlled analgesia (PCA), elastomeric, syringe, enteral, and insulin pumps. Infusion pumps are typically useful in various routes of medication delivery, including intravenously, intra-arterially, subcutaneously, intraperitoneally, in close proximity to nerves, and into an intraoperative site, epidural space or subarachnoid space.

A measure of effectiveness of infusion pumps is the startup time, or the length of time between the initiation of an infusion at a user interface of the pump and the moment that the instantaneous delivery rate actually reaches its intended steady state. Infusion pump applications that require precise, and sometimes very small, volumes of fluid to be delivered over rigidly defined durations of time are dependent not only on the ability of the delivery system to accurately achieve and consistently maintain a specific flow rate, but on the aforementioned transition or startup time.

Referring to FIG. 1, traditional infusion pumps can have significant error in delivery during the startup time, which results in safety issues such as under-delivery or over-delivery to the patient. As shown in a traditional infusion pump example of FIG. 1, in which time in minutes is depicted along the x-axis and flow rate in mL/hr is depicted along the y-axis, the actual delivery rate takes over 30 minutes to reach the target delivery rate (steady state). In other embodiments of traditional infusion pumps, this delay can last several hours or more, depending on the type of pump and/or the infusion being delivered. The total startup error of delivery rate deviation can therefore be quite large. As illustrated in the example of FIG. 1, a 0.497 mL error, or nearly 50% underdelivery, exists on a target delivery rate of 1 mL/hr. Clearly, it would be beneficial to clinicians and patients for infusion pumps to reach the target steady state level faster and in a safer manner than current pumps.

A significant factor that contributes to startup time is the drive train or network of mechanical components responsible for transmitting motive force from a motor (or other means of motion generation) to the fluid. Gearing, clutch assemblies, linkage couplings, and manufacturing or assembly tolerances all introduce varying amounts of discontinuity, "slop," and "lag," that act to prevent motive force from being rapidly or completely translated into fluid flow. Another important factor of startup time, particularly for syringe-type pumps, pertains to the time that must elapse while the pump's plunger driver increases the force applied to the syringe plunger to the point that the force overcomes opposing forces inherent in the syringe and associated tubing system and thereby begins to generate motion of the fluid therethrough. Each syringe has a "breakout force." The breakout force is the force required to break or overcome static friction ("stiction") within, or with respect to, the syringe and begin pumping fluid out of the syringe. Generally, pumps are started at the speed necessary to produce the desired steady state, which the actual delivery rate may eventually reach. Therefore, the aforementioned contributors to startup time are not considered or compensated for. As a result, significant delays in startup time, such as those depicted in FIG. 1 can result.

Traditionally, in order to manage these delays in startup time, a clinician will often initiate or prime a pump in advance of a time when delivery to a patient is needed and simply direct the fluid from the pump into a waste container or sink until the pump begins to visibly pump fluid. Such a method is not only costly and time-consuming, but dangerous to the patient who ultimately may therefore not receive an intended infusion volume.

In another example of managing a delay in startup time, because it may not always be apparent when the infusion pump has reached a steady state, a clinician may check the patient's vital signs in order to determine when the pump has begun pumping fluid. But such an analysis is distinctly disadvantageous, as the patient is being used to determine when the pump has reached a steady state. Such practice clearly raises patient safety concerns, should the pump be programmed with an incorrect rate, or an unintended medication or infuscate be unintentionally delivered.

In another example, some pumps physically stop the syringe's plunger or the pump's plunger driver, with a brake or other stopping mechanism, until the detected force exerted by the pump on the syringe plunger exceeds a given running force. At the time the detected force exceeds the running force, the plunger or the pump's plunger driver is released. Such an embodiment can result in not only unneeded wear and tear on the infusion pump and syringe hardware, but in over-delivery to the patient once the particular component is released.

Therefore, there is a need for an infusion pump that reaches the target delivery rate or steady state in minimal time, which minimizes deviation of the delivery rate from the target rate (and minimizes accuracy error by reducing the area under the delivery rate deviation curve of FIG. 1), and allows clinicians to rapidly start pump delivery without priming the pump, employing a brake, relying on patient vital sign data or other analysis, and thereby allowing the clinicians to maintain manageable and efficient workflow practices and focus more on patient care.

SUMMARY

Embodiments described or otherwise contemplated herein substantially meet the aforementioned needs. Embodiments of startup algorithms reach the targeted delivery rate or steady state in minimal time without requiring clinicians to prime the pump, employ a brake, or rely on patient vital sign data or other analysis.

In an embodiment, a method of driving an infusion pump motor comprises driving the infusion pump motor at a first rate; determining an inflection point of a sensed parameter; and driving the infusion pump motor at a second rate.

In an embodiment, an infusion pump comprises a pumping mechanism including at least one sensor and a pump motor; and a pump control subsystem configured to control operation of the pumping mechanism, the pump control subsystem including: a processor, a memory, and a startup module configured to: drive the pump motor at a first rate, receive input from the at least one sensor, and drive the pump motor at a second rate based on the input received from the at least one sensor.

In an embodiment, a closed-loop control circuit for driving an infusion pump motor comprises a proportional gain module; an integral gain module; a derivative gain module; a monitor for controlling a switchable input based on output of the proportional gain module, the integral gain module, and the derivative gain module; and a summer configured to receive the switchable input and an infusion pump motor speed and output a pump motor drive command.

In a feature and advantage of embodiments, startup algorithms effectively remove mechanical slack from the drive train of the pump and increase the force placed on the syringe plunger in a significantly shorter amount of time than if the motor simply ran at its intended rate, as is typical in conventional pumps.

In a feature and advantage of embodiments, startup algorithms control motor commands to allow for the delivery of arbitrarily complex patterns, as the evaluation and subsequent delivery is conducted in bursts or stages. Therefore, delivery based on what will be due by an arbitrary point in time makes complex patterns easier to deliver. Additionally, embodiments enable the software implemented by startup algorithms to safely transition motor control.

In a feature and advantage of embodiments, overshoot or overdelivery of fluids to patients is minimized. Embodiments provide a relatively smooth transition from startup to delivery at the desired rate.

The above summary is not intended to describe each illustrated embodiment or every implementation of the subject matter hereof. The figures and the detailed description that follow more particularly exemplify these embodiments.

BRIEF DESCRIPTION OF THE DRAWINGS

Subject matter hereof may be more completely understood in consideration of the following detailed description of various embodiments in connection with the accompanying figures, in which.

Figure 1:
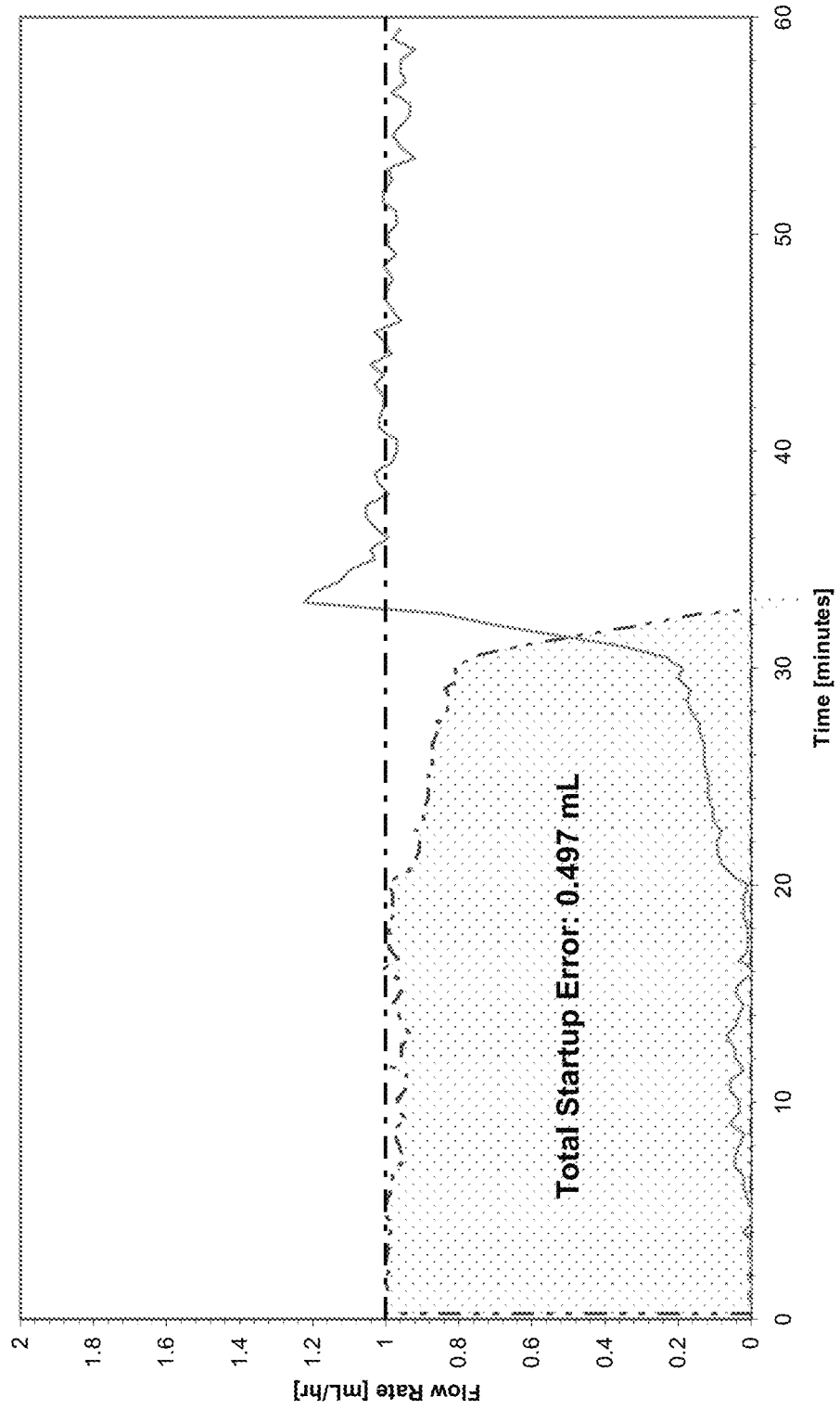
FIG. 1 is an example graph of flow rate against time depicting the deviation between actual and target delivery rates during startup conditions for a traditional infusion pump.

While embodiments are amenable to various modifications and alternative forms, specifics thereof have been shown by way of example in the drawings and will be described in detail. It should be understood, however, that the intention is not to limit subject matter hereof to the particular embodiments described. On the contrary, the intention is to cover all modifications, equivalents, and alternatives falling within the spirit and scope of subject matter hereof in accordance with the appended claims.

DETAILED DESCRIPTION OF THE DRAWINGS

Figure 2A:
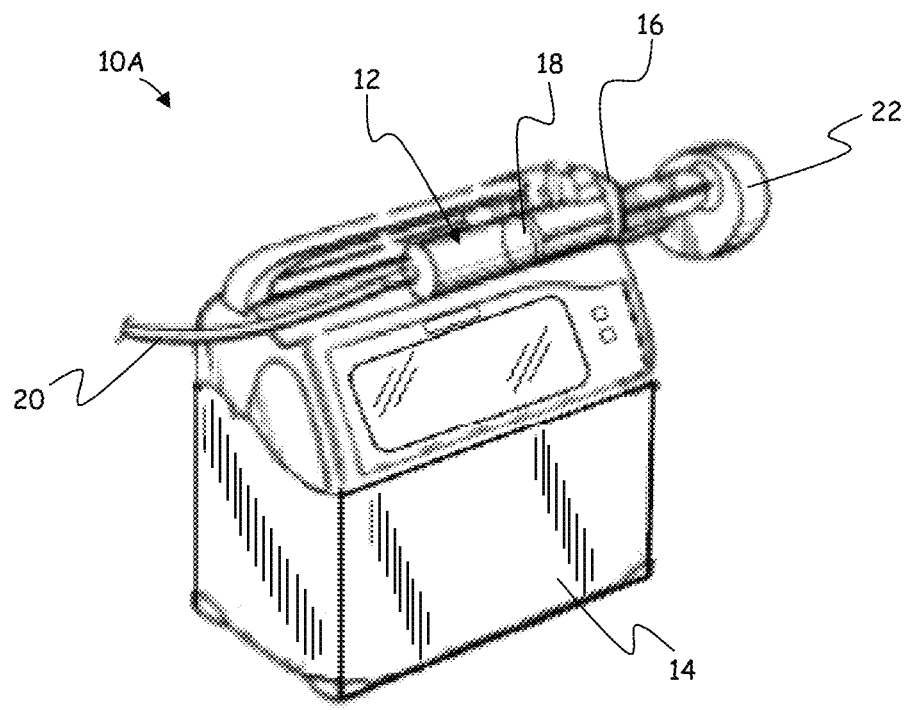
FIG. 2A is a perspective view of an example of a syringe type infusion pump, according to an embodiment.
Figure 2B:
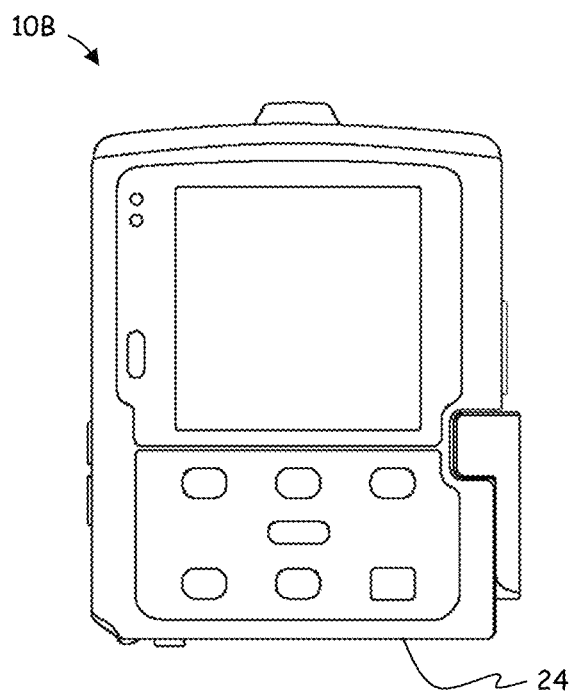
FIG. 2B is a front view of an example of an ambulatory type infusion pump, according to an embodiment.

FIGS. 2A and 2B show examples of infusion pumps 10A and 10B, respectively, (also referred to more generally in this disclosure by numeral 10), which can be used to implement embodiments of the systems and methods discussed herein. In general, infusion pump 10A is a syringe-type pump that can be used to deliver a wide range of drug therapies and treatments. Infusion pump 10A includes a pharmaceutical container or syringe 12, which is supported on and secured to housing 14 by clamp 16, respectively. In embodiments, syringe 12 can be separately supplied from pump 10A. In other embodiments, syringe 12 is an integrated component of pump 10A. Syringe 12 includes a plunger 18 that forces fluid outwardly from syringe 12 via infusion line 20 that is connected to a patient. A motor and lead screw arrangement internal to housing 14 of pump 10A cooperatively actuates a pusher or plunger driver mechanism 22, to move plunger 18. In embodiments, a sensor (schematically depicted in FIG. 3, and which is typically internal to plunger driver mechanism 22), monitors force and/or plunger position in the syringe according to system specifications.

Infusion pump 10B shown in FIG. 2B is an example of an ambulatory-type pump that can be used to deliver a wide range of drug therapies and treatments. Such ambulatory pumps can be comfortably worn by or otherwise removably coupled to a user for in-home ambulatory care by way of belts, straps, clips or other simple fastening means; and can also be alternatively provided in ambulatory pole-mounted arrangements within hospitals and other medical care facilities. Infusion pump 10B generally includes a peristaltic type infusion pump mechanism that controls the flow of medication from a reservoir (not shown in FIG. 2B) of fluid through a conduit passing along bottom surface 24 of pump 10B. This fluid can be from a cassette reservoir that is attached to the bottom of pump 10B at surface 24, or from an IV bag or other fluid source that is similarly connected to pump 10B via an adapter plate (not shown) at surface 24. Specifically, pump 10B uses valves and an expulsor located on bottom surface 24 to selectively squeeze a tube of fluid (not shown) connected to the reservoir or adapter plate to effect the movement of the fluid supplied by the reservoir, IV bag, or other fluid source, through the tube and to a patient in peristaltic pumping fashion. The embodiments of pumps of FIGS. 2A and 2B are provided only by way of example and are not intended to limit the scope of subject matter hereof. Other types of pumps and other pump configurations can be utilized in various embodiments.

Figure 3:
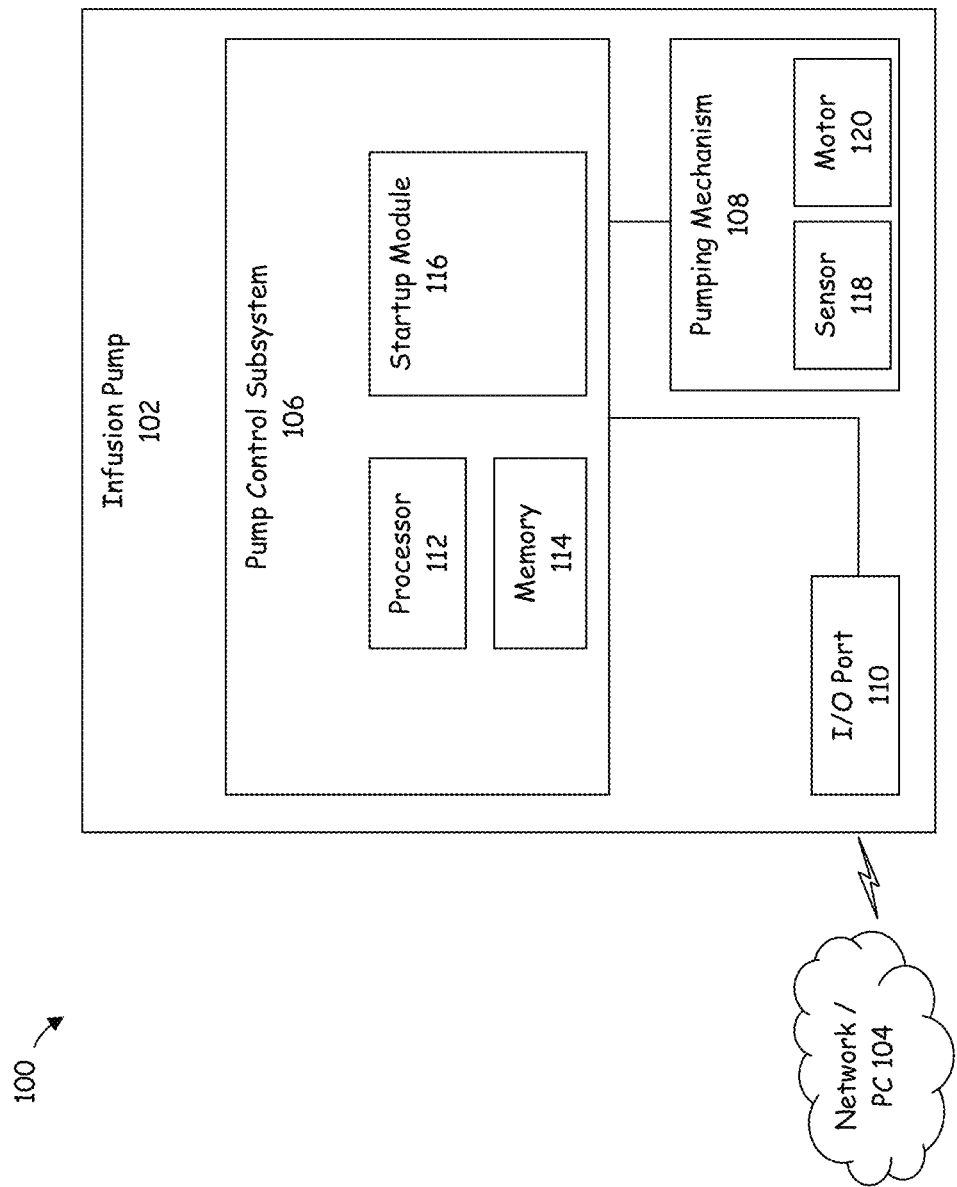
FIG. 3 is a block diagram of an infusion pump system, according to an embodiment.

Referring to FIG. 3, an infusion pump system 100 comprises, in an embodiment, infusion pump 102 (such as one of infusion pumps 10A and 10B described above). Optionally, and as depicted in FIG. 3, infusion pump 102 can be operably coupled to a network or computer 104 having software configured to interface with infusion pump 102.

In an embodiment, infusion pump 102 generally comprises pump control subsystem 106, pumping mechanism 108, and I/O port 110. Pump control subsystem 106 includes a processor 112 and memory 114 programmable with selected protocols, profiles and other settings for controlling operation of a pumping mechanism 108 such as, e.g., the aforementioned syringe and peristaltic type mechanisms. Pump control subsystem 106 further comprises startup module 116.

Processor 112 can be any suitable programmable device that accepts digital data as input, is configured to process the input according to instructions or algorithms, and provides results as outputs. In an embodiment, processor 112 can be a central processing unit (CPU) configured to carry out the instructions of a computer program. In other embodiments, processor 112 can be an Advanced RISC (Reduced Instruction Set Computing) Machine (ARM) processor or other embedded microprocessor. In other embodiments, processor 112 comprises a multi-processor cluster. Processor 112 is therefore configured to perform at least basic selected arithmetical, logical, and input/output operations.

Memory 114 can comprise volatile or non-volatile memory as required by the coupled processor 112 to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing examples in no way limit the type of memory that can be used, as these embodiments are given only by way of example and are not intended to limit subject matter hereof.

Startup module 116 comprises algorithms or instructions for startup of infusion pump 102, as will be described further below. As depicted, startup module 116 can be implemented as part of pump control subsystem 106 by utilizing processor 112 and memory 114. In other embodiments (not shown), startup module 116 can be implemented by a processor and memory separate from pump control subsystem 106, processor 112 and memory 114.

In embodiments, pumping mechanism 108 comprises a sensor 118 and a motor 120 and is operably coupled to one or more internal or external reservoirs, IV bags, or other fluid sources.

In an embodiment, sensor 118 is configured to monitor force. For example, in embodiments described above, wherein infusion pump 102 is a syringe pump such as infusion pump 10A having syringe 12 that includes plunger 18 that forces fluid outwardly from syringe 12 via infusion line 20 that is connected to a patient, sensor 118 can be located at the point where mechanism 22 of infusion pump 102 contacts plunger 18 of syringe 12 in order to measure the force imparted by one on the other. In embodiments, sensor 118 can be located at other locations within, or outside of, mechanism 22. Sensor 118 can comprise a force sensor, pressure sensor, distance sensor or any other suitable sensor. In other embodiments, pumping mechanism 108 comprises one or more additional sensors 118. In embodiments, sensor 118 can also be used to determine occlusion within syringe 12 and/or infusion line 20.

Figure 4A:
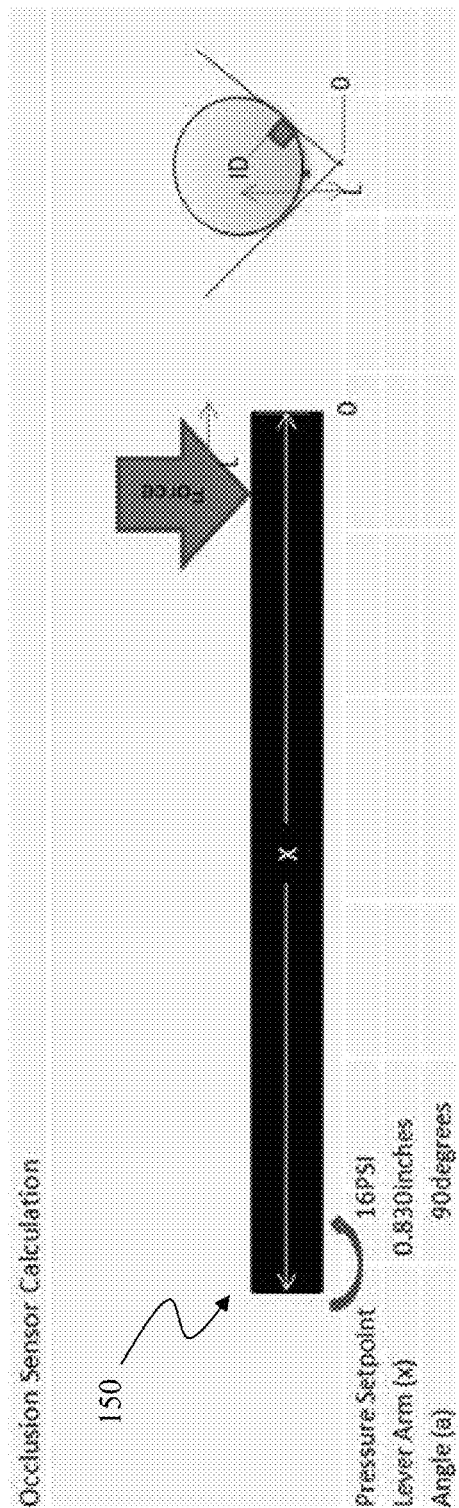
FIG. 4A is a diagram of a force sensor bending movement, according to an embodiment.
Figure 4B:
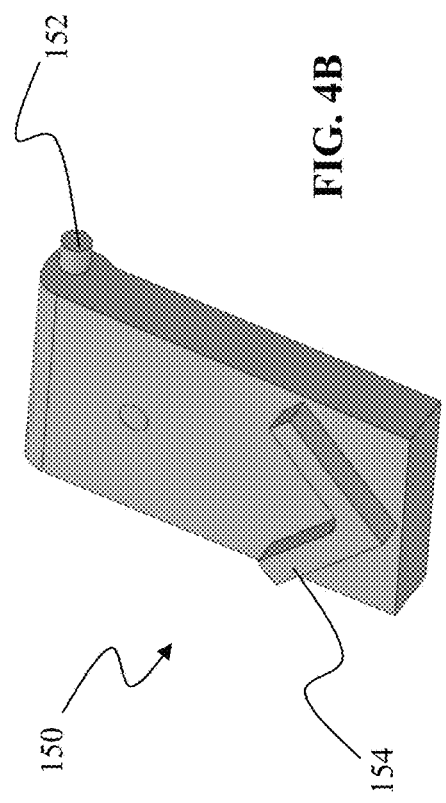
FIG. 4B is a perspective view of a force sensor component, according to an embodiment.

Referring to FIGS. 4A and 4B, an embodiment of a force sensor 150 utilizing a lever arm is depicted. In embodiments, force sensor 150 can detect fluid flow, lack of fluid flow (i.e., because of an occlusion) or other force or movement based on force imparted on force sensor 150. For example, in one embodiment a thumbpress of a syringe plunger can be arranged against, adjacent, or otherwise proximate force sensor 150 that is incorporated in pump 10A by way of a pivotable coupling (not illustrated) of post or pin 152 with drive mechanism 22. Although not illustrated, it is to be understood that in this example, the plunger's thumbpress would be positioned to reside in V-slot 154 of sensor 150. When drive mechanism 22 exerts force against the syringe's thumbpress, in operation of pump 10A, a force is correspondingly exerted against force sensor 150. It is to be appreciated that a smaller diameter thumbpress—of a correspondingly smaller diameter and thus smaller volume syringe—will advantageously result in a larger force sensed at sensor 150 in lever fashion since such force is imparted at a distance that is farther from post or pin 152 than would occur with a larger thumbpress of a larger syringe. As such, smaller operative forces attributable to smaller syringes can be as reliably sensed as larger forces attributable to larger syringes. This variable pivoting of sensor 150, depending upon the size of the syringe thumbpress, can be detected and the corresponding force sensed by, e.g., a capacitive, piezoelectric, resistive, or other suitable effect component. Generally, such a force sensor system can be employed as described in published PCT Publication No. WO 2013/177379, entitled "Occlusion Detection."

Referring again to FIG. 3, motor 120 is configured to drive fluid from one or more internal or external reservoirs, IV bags, or other fluid sources, to the patient. For example, in embodiments described above, motor 120 and a lead screw arrangement internal to housing 14 of pump 10A cooperatively actuates a pusher or plunger driver mechanism 22, to move plunger 18. Motor 120 can therefore comprise any suitable drive mechanism.

Infusion pump 102 can further include a USB port, wireless interface, or other appropriate input/output (I/O) interface port 110 for connecting infusion pump 102 to network or computer 104 having software configured to interface with infusion pump 102. In embodiments, network or computer 104 can transmit, via interface port 110, updated software or algorithms for pump control subsystem 106, and in particular, startup module 116. Power to infusion pump 102 is accomplished via an AC power cord and/or internally provided battery.

In embodiments, startup module 116 is configured to utilize information provided by sensor 118 to regulate motor 120 rate in an informed, active, and substantially real-time manner that dramatically improves the performance of infusion pump 102.

Figure 5:
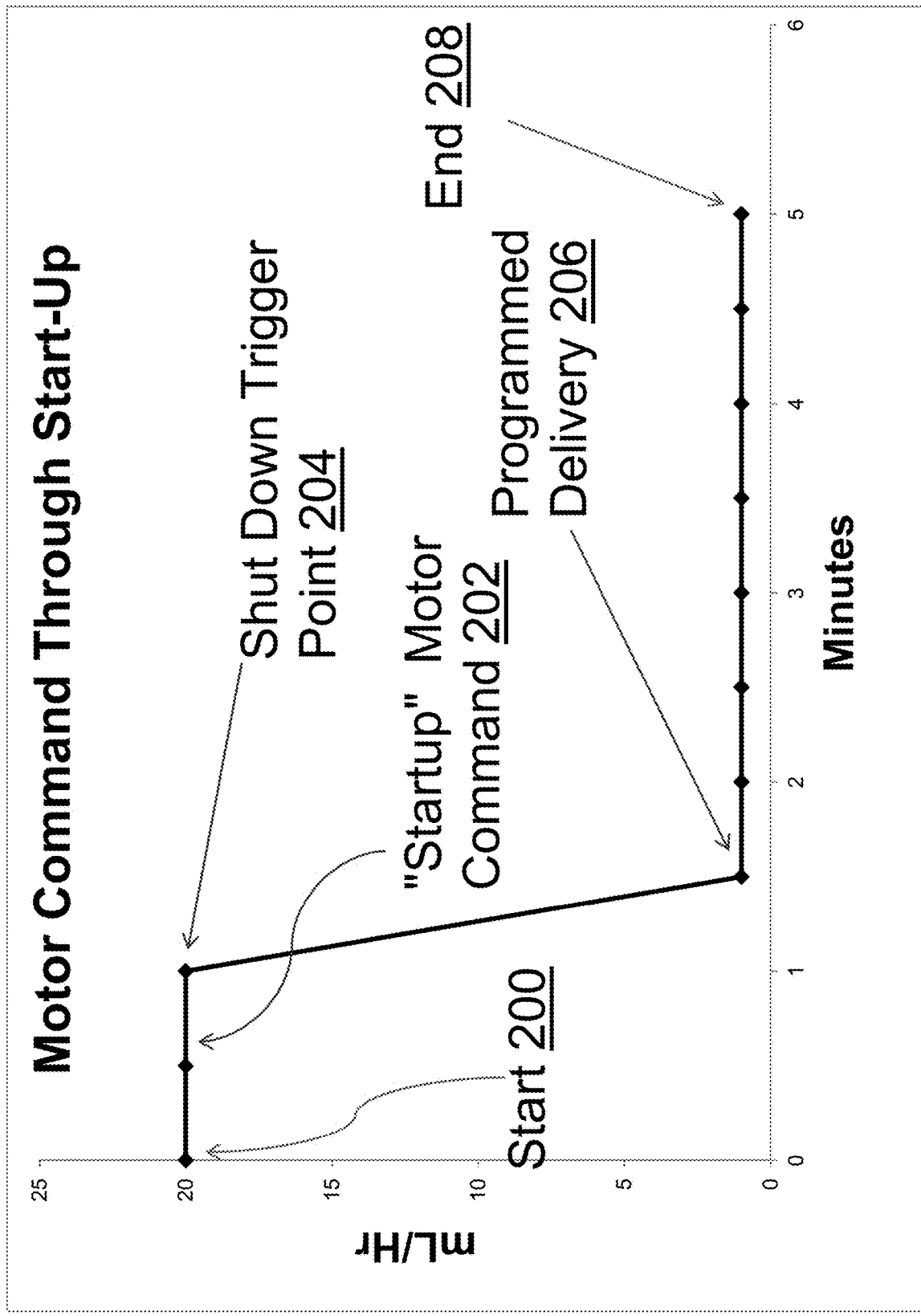
FIG. 5 is a graph of flow rate with respect to time, depicting a pump motor command through startup, according to an embodiment.

For example, referring to FIG. 5, an example of a graph of flow rate with respect to time for an embodiment of a motor command through startup is generally depicted. Time is depicted along the x-axis and flow rate in mL/hr is depicted along the y-axis. At start 200, a flow rate begins at time 0. As depicted, the flow rate begins at a rate greater than 0 because of embodiments of startup motor command 202, as will be described further below. Embodiments of startup motor command 202 can be issued immediately after pump power-on, in embodiments, or as soon as the hardware and software will accept such command. Therefore, as depicted, startup motor command 202 is run throughout startup until shut down trigger point 204. In embodiments, the transition from startup motor command 202 to shut down trigger point 204 can be, for example, stepped, curved, sinusoidal, decreasing, a function of force, a function of force velocity, a function of force acceleration, or multiple triggers in combination. At shut down trigger point 204, startup motor command 202 is exited or terminated. In embodiments, a "stop" or "shutdown" command is given. In other embodiments, a startup algorithm operating within or in cooperation with command 202 exits or terminates due to one or more measured values (such as those provided by sensor 118) between, e.g., pump 102 and mechanism 108 in FIG. 3. In other embodiments, the startup algorithm exits or terminates due to normal exit or termination conditions of the algorithm. At programmed delivery 206, the pump begins typical programmed delivery, according to the pump protocol. At end 208, the pump exits or terminates its typical programmed delivery. Therefore, in general, as illustrated by FIG. 5, a startup command to a pump motor is introduced, and subsequently, the flow is transitioned at a trigger point to commanded, programmed delivery.

Figure 6:
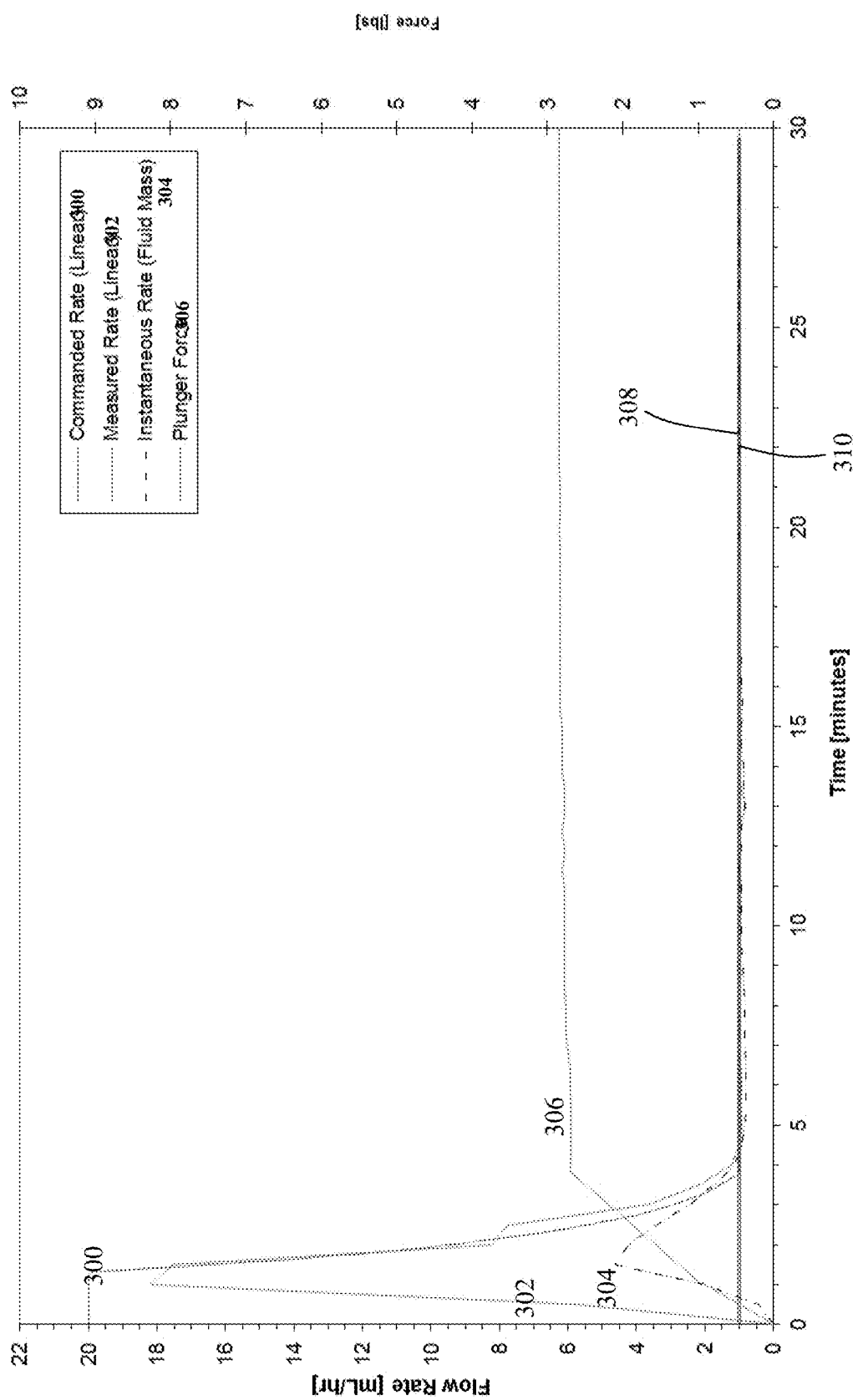
FIG. 6 is a graph of flow rate and force with respect to time, depicting a shortened time to steady state delivery, according to an embodiment.

Referring to FIG. 6, the results of an implementation of an embodiment of a motor command through startup, for example, the motor command through startup algorithm illustrated by FIG. 5, is depicted. The results of FIG. 6 are in contrast to the problem illustrated by FIG. 1. In other words, the flow rate curve of flow rate and plunger force with respect to time are illustrated when embodiments of startup algorithms are implemented according to subject matter hereof. Time is depicted along the x-axis. Flow rate in mL/hr is depicted along one y-axis, and force is depicted along the opposite y-axis.

Commanded rate 300 comprises a linear rate depicting the motor speed commanded by the startup algorithm. Measured rate 302 comprises a measured linear rate. Instantaneous rate 304 comprises the instantaneous linear rate of a fluid mass actually delivered. Plunger force 306 comprises the force measured by, for example, sensor 118. According to embodiments of a motor command through startup algorithm, the time elapsed until the measured (linear) rate 302 and the instantaneous rate 304 reach their respective steady states is greatly reduced when compared to the elapsed time of FIG. 1. Likewise, upper error 308 and lower error 310 are minimized when compared to, e.g., FIG. 1. Plunger force 306 is shown and transitions from a generally increasing force from about time=0 minutes to about time=4 minutes, and then to a generally constant force thereafter. In embodiments of startup algorithms according to subject matter hereof, the startup sequence is entered at time=0 minutes and generally exited or terminated at about time=4 minutes as the steady state is reached and the pump transitions to programmed delivery. It is to be appreciated and understood, however, that the steady state time depicted in the example of FIG. 6, about 4 minutes, will vary depending upon particular parameters and characteristics of a specific embodiment. Thus, for example, use of relatively larger syringes of relatively larger volumes may result in correspondingly greater times to reach steady state. As illustrated, in an embodiment of a motor command startup algorithm, when compared to the deviation between actual and target delivery rates during startup conditions for a traditional infusion pump, the startup error is cut by 8 fold, from 0.497 mL to 0.067 mL. In embodiments, the startup error can be reduced or cut by more or less than the example depicted in FIG. 6, depending on the application, hardware, and startup algorithm, among other factors.

Motor Rate Startup Algorithm

Figure 7:
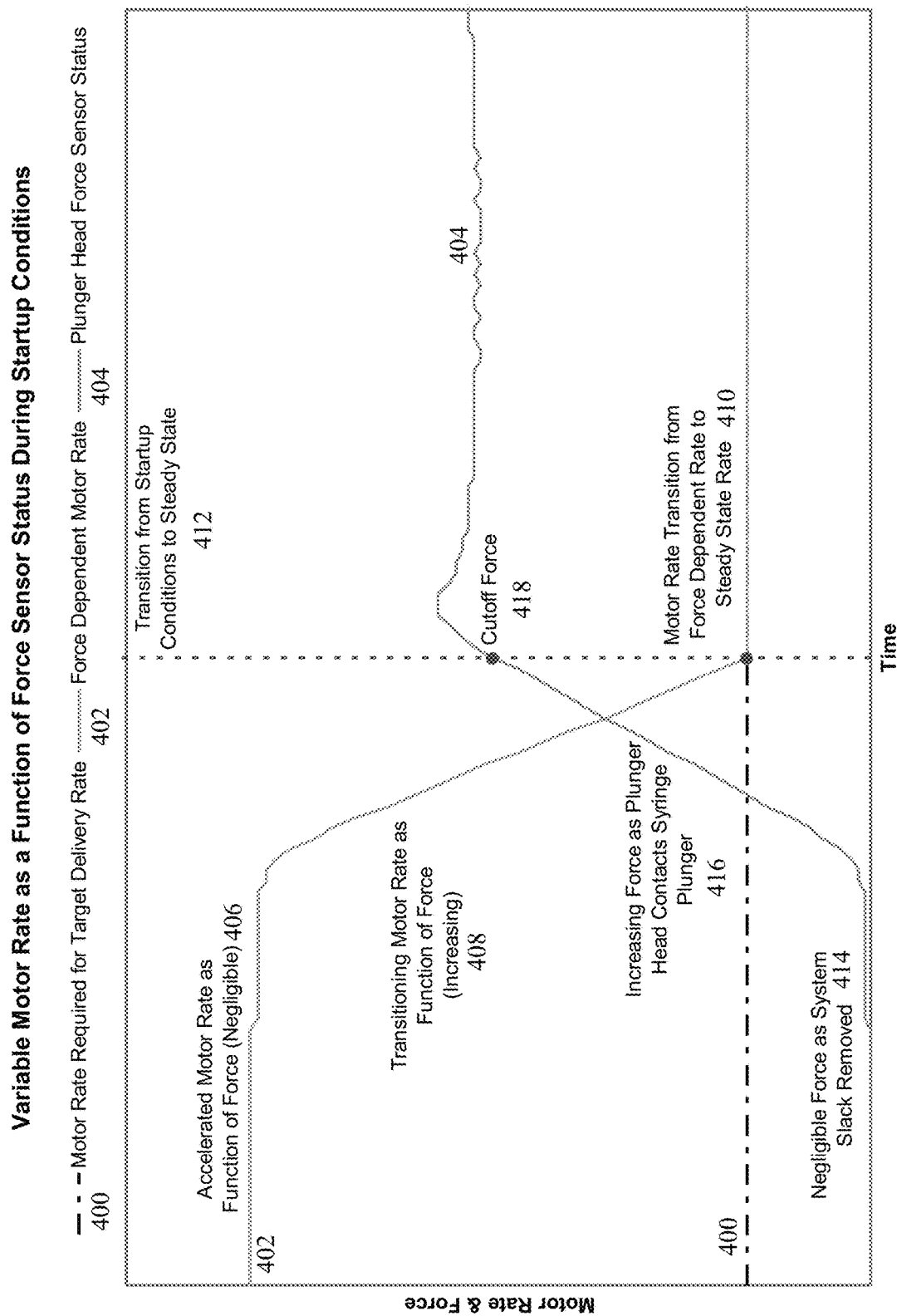
FIG. 7 is a graph of pump motor rate and force with respect to time, during startup conditions and illustrating a motor rate algorithm according to an embodiment.

Referring to FIG. 7, an illustration of a motor rate startup algorithm is depicted, according to an embodiment of subject matter hereof and in an example utilizing a syringe pump. Time is depicted along the x-axis, and motor rate and plunger head force are depicted along the y-axis. The motor rate required for target delivery rate 400 is illustrated as a substantially constant horizontal line. In embodiments, the motor rate required for target delivery rate 400 is the steady state rate at which programmed delivery is desired.

Force-dependent motor rate 402 and the plunger head force sensor status 404 are interrelated, as depicted in FIG. 7. In an embodiment, force-dependent motor rate 402 is initially configured for an accelerated motor rate 406 (in embodiments, as a function of the force sensed, as depicted by plunger head force sensor status 404, and as will be described). In embodiments, an initial accelerated motor rate 406 can be any appropriate rate according to the particular pump hardware in use. During this stage, the plunger head force is negligible. This period of accelerated motor rate 406 removes mechanical slack from the drive train of the pump and increases the force placed on the syringe plunger in a significantly shorter amount of time than if the motor simply ran at its intended rate (e.g. target delivery rate 400). This shortened time is particularly apparent when using extremely slow rates which may be needed to produce deliberate fluid delivery rates typical of pediatric care or when highly potent drugs are involved. In embodiments, for example, the plunger-driven infusion pump of pump 10A, during the period of accelerated motor rate 406, the motor (for example, motor 120) therefore advances the pump plunger (for example, plunger 18) at an accelerated rate until the force applied to the plunger reaches the magnitude required to overcome opposing forces (e.g., inertial, static friction, back pressure). In an embodiment, force-dependent motor rate 402 then transitions to the rate appropriate for the intended fluid delivery rate, as depicted by transitioning motor rate as a function of force 408 (which is decreasing, and will be described below). At the time where the pump transitions from startup conditions to steady state 412, the motor rate has transitioned from a force-dependent rate to a steady state rate 410.

With respect to the plunger head force, embodiments can include the force sensed by sensor 118 in FIG. 3. The plunger head force sensor status 404 is initially negligible, as shown by the plunger head force sensor status 404 segment labeled "Negligible Force as System Slack Removed 414." During pump startup, there is increasing force at 416 as, for example mechanism 22 in FIG. 2A contacts plunger 18. This increasing force is necessarily related to the transitioning motor rate as a function of force 408, as described above, and as shown in FIG. 7. At the time where the pump transitions from startup conditions to steady state 412, a cutoff force 418 is detected, sensed, or otherwise determined by the sensor (e.g. sensor 118 in FIG. 3). Subsequently, as described with respect to the force-dependent motor rate 402, the motor rate transitions from a force-dependent rate to a steady state rate 410. Likewise, plunger head force sensor status 404 transitions to a steadily-sensed force. In embodiments, sensor 118 can then be used for ongoing steady-state programmed delivery functions, such as occlusion sensing, as the startup algorithm sequence concludes.

Figure 8:
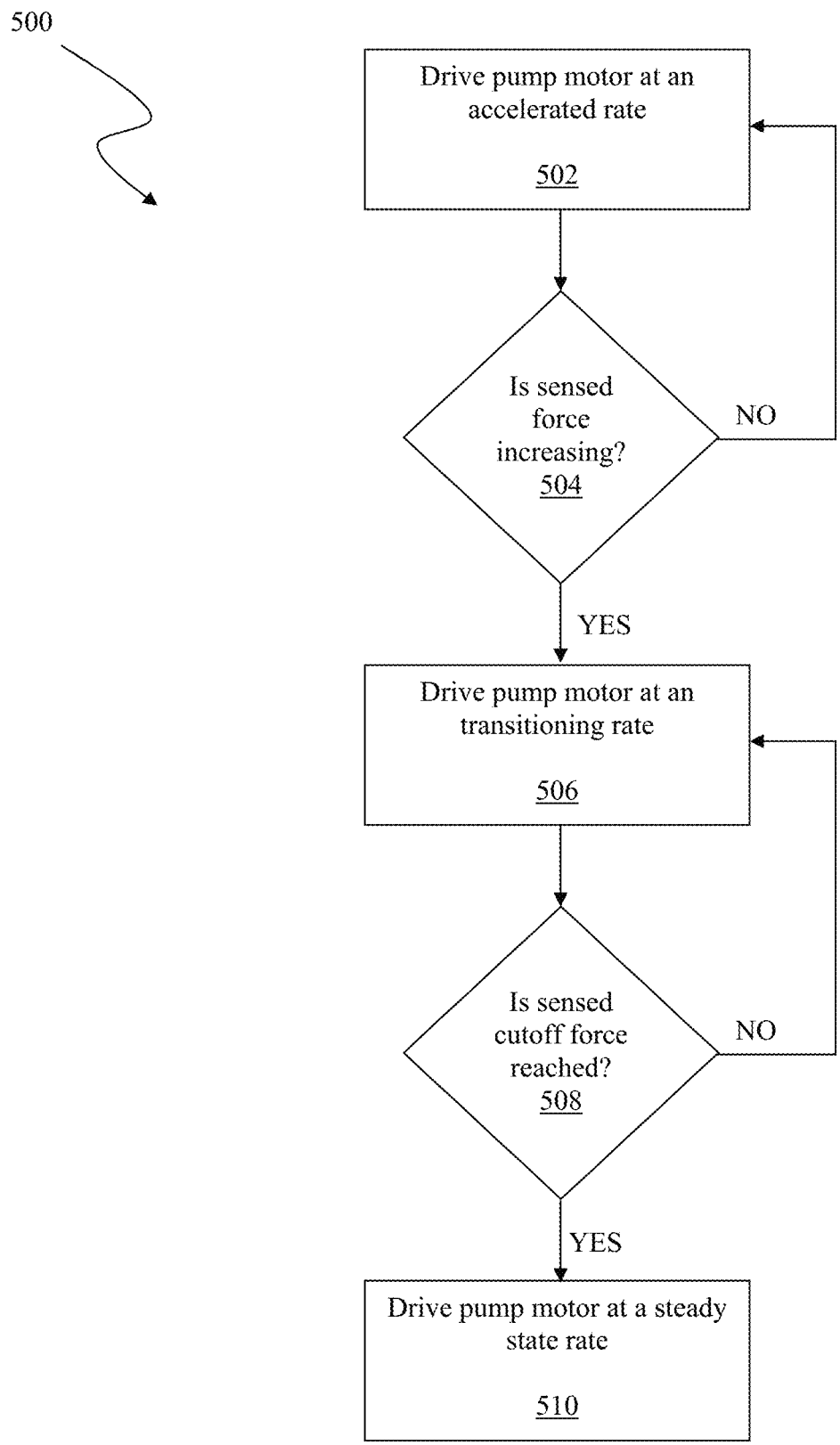
FIG. 8 is a flowchart of a motor rate algorithm, according to an embodiment.

For example, referring to FIG. 8, a flowchart of an embodiment of a motor rate startup algorithm 500 is illustrated. Embodiments of motor rate startup algorithm 500 can be implemented by, for example, and referring to FIG. 3, pumping mechanism 108 as directed by, for example, pump control subsystem 106 and startup module 116.

At 502, the pump motor is driven at an accelerated rate. At decision point 504, it is determined whether the force sensed by sensor 118 is increasing. If the sensed force is not increasing, motor 120 continues to be driven at an accelerated rate at 502. If, at decision point 504, the sensed force is determined to be increasing, motor 120 transitions to a transitioning rate at 506. In embodiments, the transitioning rate can be a lower rate due to the removal of system slack and the plunger driver mechanism contacting the syringe plunger. In embodiments, motor 120 is driven at a transitioning rate at 506 that is analogous to transitioning rate 408 in FIG. 7. At decision point 508, it is determined whether the force sensed by sensor 118 has reached the cutoff force. If the sensed force has not reached the cutoff force, motor 120 continues to be driven at the transitioning rate. If, at decision point 508, the sensed force has reached the cutoff force, motor 120 moves to a steady state rate at 510.

In embodiments, the force sensed by sensor 118 is provided continuously, or substantially in real-time, to, for example, pumping mechanism 108 in order to variably control motor 120. As such, decision points 504 and 508 can be implemented not as discrete decision points, but thresholds to be reached. One skilled in the art will readily appreciate the possibilities for implementation of motor rate startup algorithm 500. The example provided by FIG. 7 is intended to be illustrative of an embodiment given only by way of example and is not intended to limit the scope of subject matter hereof.

State Identification Startup Algorithm

In an embodiment, a pump startup algorithm is configured to identify a plurality of startup states. By utilizing the correlation between various pumping characteristics, such as actual delivery rate, expected delivery rate, and force sensor status, among others, startup states can be identified. The pump motor can be controlled depending on the current state. In embodiments, known future states can also be considered and included for determinations of motor control. In embodiments, past states can also be considered and included for determinations of motor control.

Figure 9:
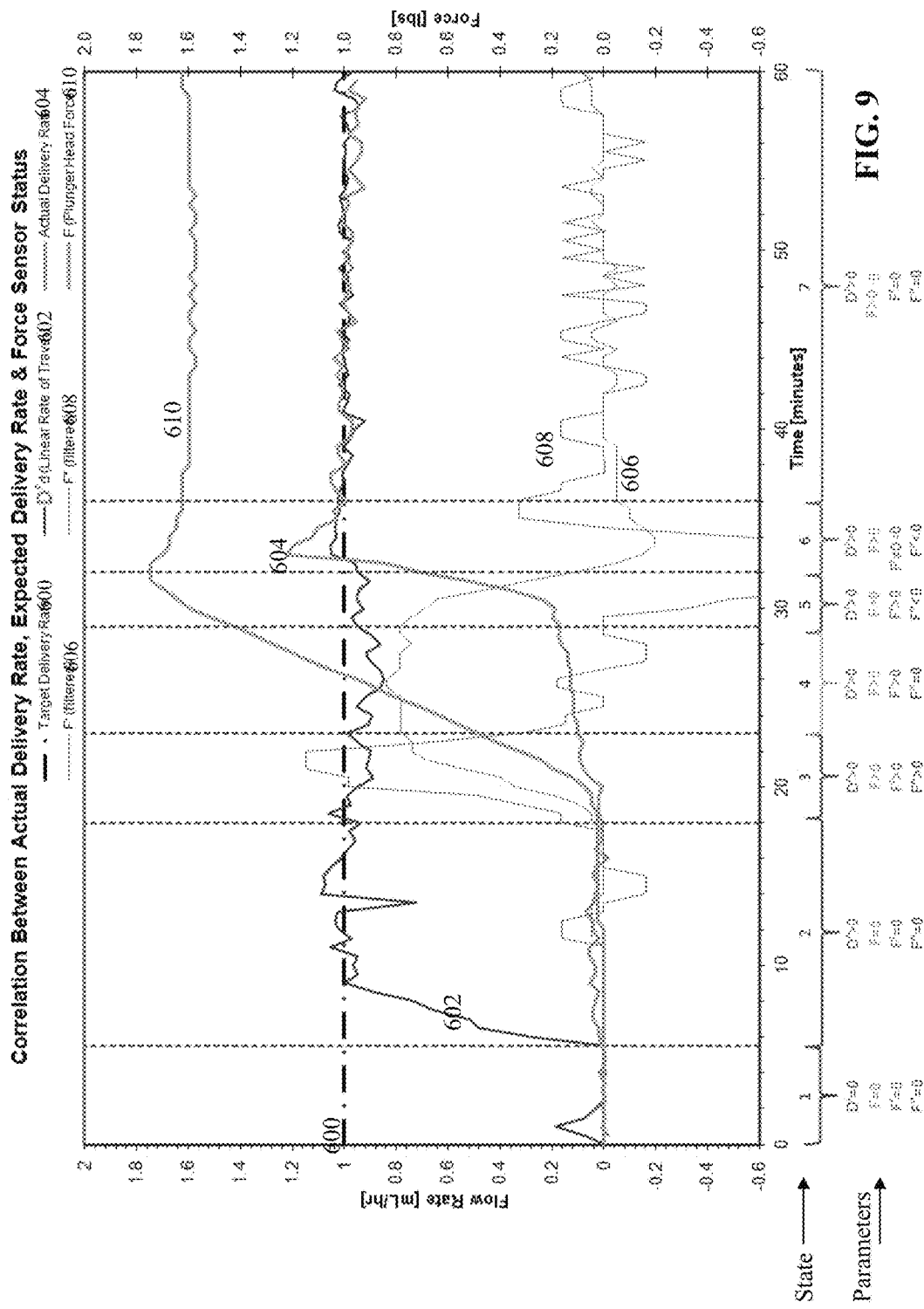
FIG. 9 is an annotated graph of motor rate and force with respect to time, during startup conditions illustrating a state identification startup algorithm, according to an embodiment.

Referring to FIG. 9, an annotated graph of the correlation between actual delivery rate, expected delivery rate and force sensor status is depicted, according to an embodiment. Time in minutes is depicted along the x-axis. Flow rate in mL/hr is depicted along one y-axis, and force is depicted along the opposite y-axis. Additionally, the respective startup segments or states and the corresponding parameters are identified along the x-axis. Target delivery rate 600 is depicted at 1 mL/hr as a horizontal line across FIG. 9. Target delivery rate 600 is the steady state rate at which the delivery is desired. The curves of the plunger linear rate of travel 602, actual delivery rate 604, plunger head force 610, plunger head force velocity 606, and plunger head force acceleration 608 are also depicted, and will be described further below. As referenced throughout this document, the term "plunger head force" pertains to a force exerted by, for example, plunger driver mechanism 22 on plunger 18, and may be sensed and measured by, for example, sensor 118. As depicted in FIG. 9, plunger linear rate of travel 602 has been scaled up according to the cross-section of the syringe to provide a more meaningful illustration, and is not to scale.

Referring to Table 1 below, in an example of a syringe pump embodiment of subject matter hereof, each of the individual startup states has a group of parameter values unique to the respective state. In an embodiment, the group of parameters is {D', F, F', F'' }, where D' is the linear rate of travel, F is the plunger head force, F' is the plunger head force velocity, and F'' is the plunger head force acceleration. In other embodiments, other, additional, or fewer parameters are utilized, according to the particular application and startup goals. In the example embodiment of Table 1 below, the respective states are determined based on the parameters' values with respect to 0 (including positive or negative indications). In embodiments, the respective states can be determined not only by the group of parameter values with respect to 0, but alternatively or additionally based on other threshold values. In other embodiments, additional or fewer startup states can be defined and utilized, according to the respective embodiments and modes of operation.

TABLE 1

State Identification Startup Algorithm States, Description, and Parameters

| State | Description | Parameters |
|---|---|---|
| 1 | Internal Slack - Backlash, Gear Lash, Thread Tolerances are still potential factors and the system is not physically moving | D' = 0<br>F = 0<br>F' = 0<br>F'' = 0 |
| 2 | External Slack - The plunger driver mechanism has not yet come into contact with the syringe plunger | D' > 0<br>F = 0<br>F' = 0<br>F'' = 0 |
| 3 | Initiate Preload - The plunger driver mechanism is making contact with the syringe plunger | D' > 0<br>F > 0<br>F' > 0<br>F'' > 0 |
| 4 | Preload - The plunger driver mechanism is imparting a force on the syringe plunger | D' > 0<br>F > 0<br>F' > 0<br>F'' = 0 |
| 5 | Stiction - The force being applied by the plunger driver mechanism is beginning to overcome the force of static friction between the plunger and the syringe | D' > 0<br>F > 0<br>F' > 0<br>F'' < 0 |

TABLE 1-continued

State Identification Startup Algorithm States,
Description, and Parameters

| State | Description | Parameters |
|---|---|---|
| 6 | Motion - The force needed to overcome static friction has been exceeded and the syringe plunger has moved forward | D' > 0<br>F > 0<br>F'≠0<br>F" < 0 |
| 7 | Steady State - The system has reached delivery equilibrium | D' > 0<br>F >= 0<br>F' = 0<br>F" = 0 |

In State 1, the pump is in a state of "internal slack." D', F, F', and F" are all 0. There is no movement of the pump motor or plunger. In embodiments of State 1, backlash, gear lash, thread tolerances, gearing, clutch assemblies, linkage couplings, and/or manufacturing or assembly tolerances, for example, are present and have yet to be removed or exceeded to enable plunger movement. In embodiments, the length or duration of State 1 is pump-dependent, in that the unique characteristics of the pump affect the ability of the plunger to move.

In State 2, the pump is in a state of "external slack." D' is greater than 0, indicating that the internal slack of State 1 has been removed. In an embodiment, a linear potentiometer can be monitored such that the pump (for example, pump control subsystem 106), can determine when the potentiometer has begun changing value. According to embodiments, one skilled in the art will recognize that the "monitoring" can also be by measurement of linear position and/or velocity. In other embodiments, a system utilizing derived values can be implemented. For example, a linear sensor can be omitted and replaced with a derived signal such as a calculated linear value that is based on the rotation of the motor. In embodiments, the rotation can be monitored with a rotary-type sensor and encoder (closed loop) or with a stepper motor capable of running in an open loop mode (without an encoder). In embodiments of State 2, the plunger driver mechanism has not yet come into contact with the syringe plunger. As a result, F, F', and F" all remain 0. In embodiments, the length or duration of State 2 is operator-dependent, in that linear rate of travel of the plunger can be determined by the operator.

In State 3, the pump is in a state of "initiate preload." D', F, and force-related derivatives F' and F" are all greater than 0. In embodiments of State 3, the plunger driver mechanism is making contact with the syringe plunger. In embodiments, the length or duration of State 3 is both pump-dependent and operator-dependent.

In State 4, the pump is in a state of "preload." D', F, and F' all remain greater than 0. However, F" is equal to 0, as there is no more plunger head force 610 acceleration, and the plunger is instead increasing velocity at a constant rate. In embodiments of State 4, the plunger driver mechanism is imparting a force on the syringe plunger.

In State 5, the plunger experiences static friction or "stiction" within, or with respect to, the syringe. D', F, and F' all remain greater than 0. However, the force acceleration F" is negative. In embodiments of State 5, the resulting negative acceleration is due to the force being applied by the plunger driver mechanism to overcome the aforementioned stiction.

In State 6, the pump is in a state of "motion." D' and F remain greater than 0. F" remains negative. However, F' is nonzero. In embodiments of State 6, the force needed to overcome stiction has been exceeded and the syringe plunger has moved forward. The force in State 6 is so great as to overcome stiction and transition to plunger motion, but then falls off as the plunger moves as desired pump begins to deliver. Newton's First Law of Motion states that a body at rest will remain at rest unless an outside force acts on it, and a body in motion at a constant velocity will remain in motion in a straight line unless acted upon by an outside force. As a result, the maximum amount of force required to move an object occurs at the point where motion first starts. In embodiments, this point is State 6.

In State 7, the pump is in a state of "steady state." In embodiments of State 7, the system has reached equilibrium. D' and F are both greater than 0; but F' and F" both equal 0. In embodiments, F' and/or F" are roughly equal to 0 due to a level of "noise" or external interference caused by, for example, surface roughness or inconsistent lubrication, etc. At this point, the pump has transitioned through its startup algorithm and is pumping according to the steady state rate at which programmed delivery is desired.

In another embodiment, the entire startup sequence can be effectively moved up one state. For example, time 0 can be the point at which the potentiometer is positive, thereby indicating that the pump has started. State 1 can thus be eliminated, as embodiments of a startup algorithm can be instantiated or initialized after the potentiometer is determined to be positive (and the pump started). In other embodiments of a startup algorithm, the method can be programmed to wait until the positive potentiometer point has been reached before proceeding to other states. The startup sequence can therefore be further shortened and made more efficient.

In embodiments, startup algorithms according to the subject matter disclosed herein can stop or decrease the rate of pump motor or plunger motion at any of the state conditions or within any of the state conditions. In an embodiment, "stopping" the rate of pump motor or plunger motion comprises stopping the scaled up rate of the motion so that the plunger is no longer accelerating. For example, the shut down trigger point can be at state 4, when the pump is in a state of "preload." In another embodiment, the shut down trigger point can be at state 5, when the plunger experiences static friction or "stiction" within, or with respect to, the syringe. In another embodiment, the shut down trigger point can be at state 6, when the pump is in a state of "motion." Effectively, referring again to FIG. 9, target delivery rate 600 is adjusted based on the measured feedback of plunger head force 610 and/or the derived values of plunger head force velocity 606 and plunger head force acceleration 608, according to their respective parameters within the state conditions.

Figure 10:
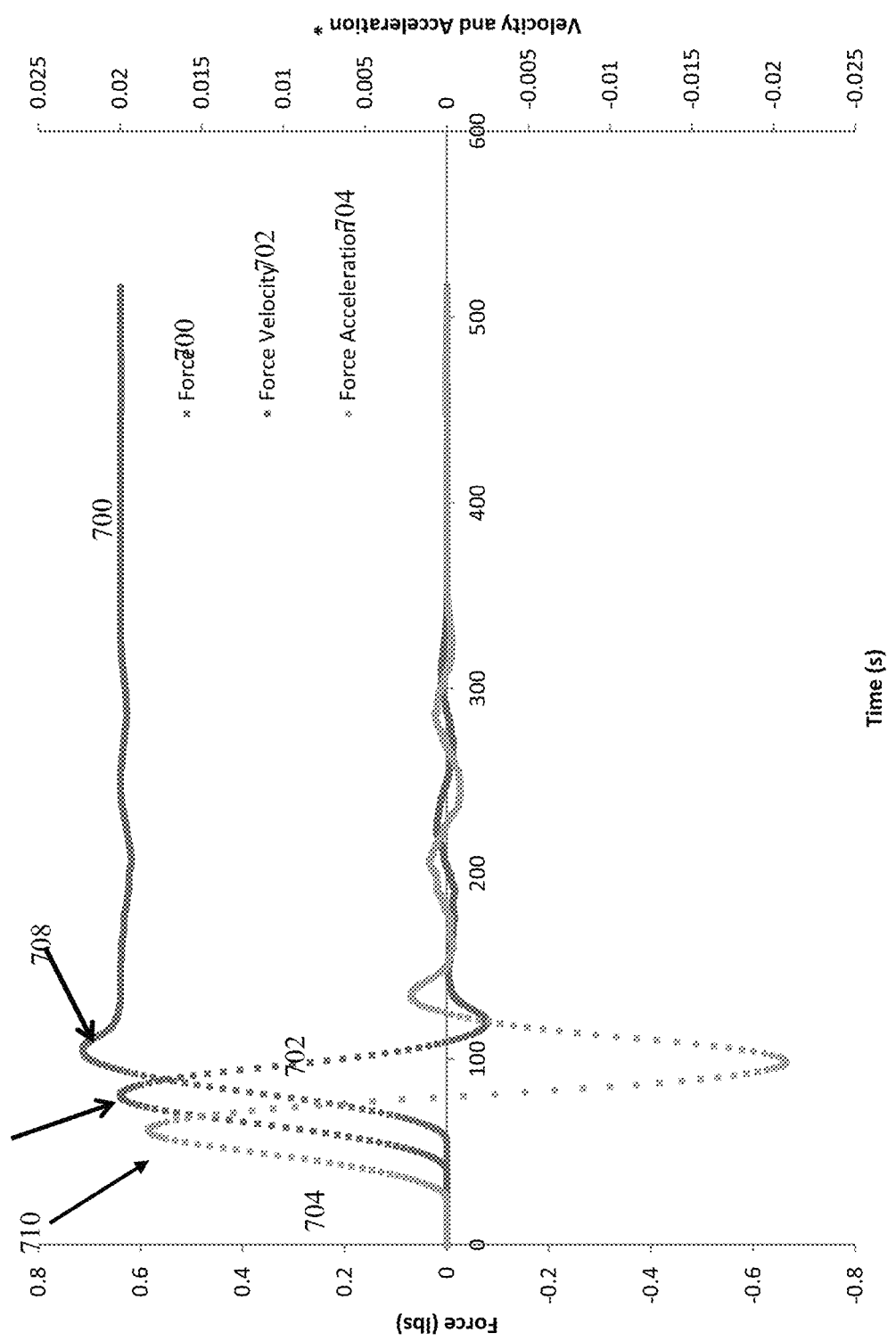
FIG. 10 is a graph of force, force velocity, and force acceleration with respect to time, during startup conditions for a state identification startup algorithm, according to an embodiment.

Referring to FIG. 10, an example startup sequence of the force curve for a pump is illustrated. Time in seconds is depicted along the x-axis. Force in lbs is depicted along one y-axis, and velocity and acceleration are depicted along the opposite y-axis. In the example of FIG. 10, the startup curve is illustrative of a 20 mL/hr, 60 cc syringe system. Force velocity 702 was obtained by: $\Delta F/\Delta t$ (change in force 700 over change in time), and force acceleration 704 was calculated using: $\Delta F'/\Delta t$ (change in force velocity 702 over change in time). Note that the force acceleration 704 magnitude was amplified by a factor of 30 to allow it to be placed on the same axes as force velocity 702, for the sake of comparison.

As shown, by plotting the first and second derivatives of force 700, $\Delta F/\Delta t$ and $\Delta F'/\Delta t$ respectively, important transition or inflection points in the force can be seen. The peaks in force velocity 702 show inflection points within force 700, where the force 700 transitions between increasing and decreasing rates. In embodiments, startup algorithms can utilize one or more of the inflection points of force velocity 702 or force acceleration 704 as an indicator to change motor speed in order to minimize or perhaps even prevent overshoot of delivery at 708. Embodiments therefore result in quick startup with a smooth transition to steady state at the desired delivery rate.

In embodiments of startup algorithms, the motor speed is commanded to decrease after the chosen inflection point as a function of either velocity or acceleration, or combinations thereof, where appropriate. For example, if the first peak 706 of the force velocity 702 was chosen as the point to start decreasing speed, the motor speed then decreases over time according to the absolute value of the velocity. In another embodiment, a trigger switch point for the motor drive can be at the negative point of force acceleration 704. In this example, the trigger switch point would be inflection point 710 of force acceleration 704.

Figure 11:
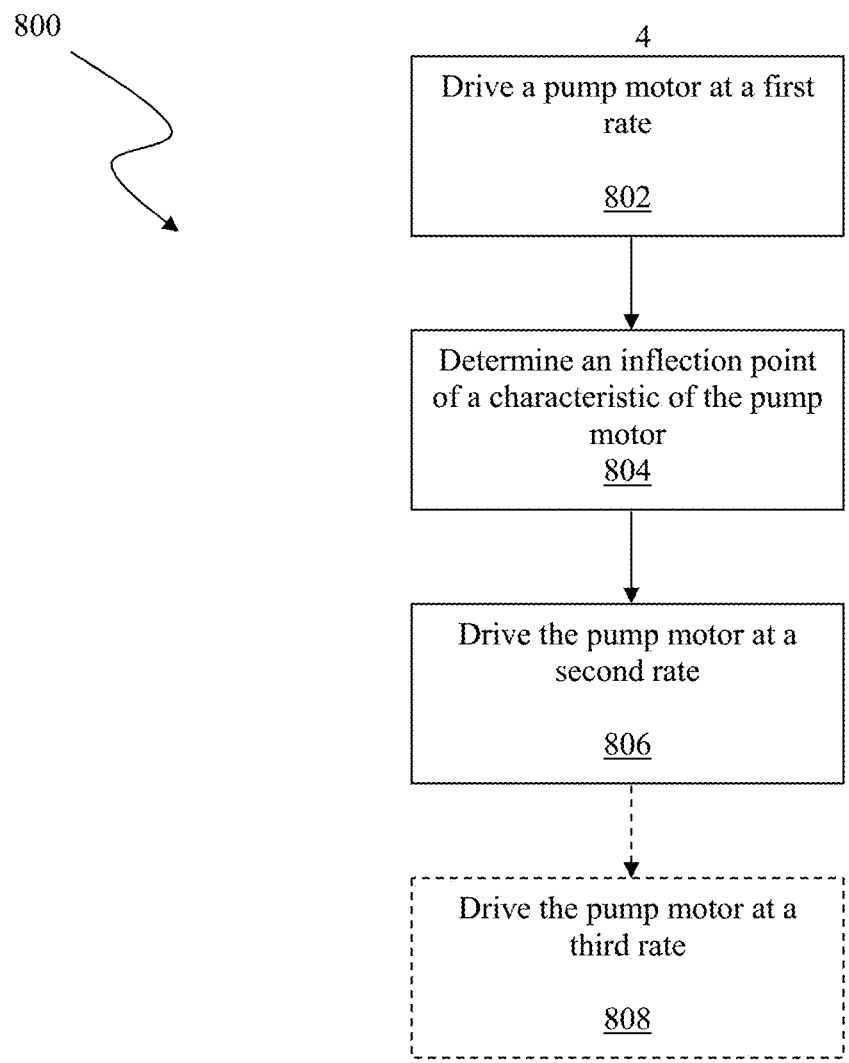
FIG. 11 is a flowchart of a startup algorithm, according to an embodiment.

Referring to FIG. 11, a flowchart of an embodiment of a startup algorithm 800 is illustrated. Embodiments of startup algorithm 800 can be implemented by, for example, and referring to FIG. 3, pumping mechanism 108 as directed by, for example, pump control subsystem 106 and startup module 116.

At 802, the infusion pump motor, for example, motor 120, is driven at a first rate. In embodiments, the first rate can be an accelerated rate; for example, that discussed with respect to FIG. 8.

At 804, a determination of an inflection point for a characteristic of the pump motor is made. In embodiments, as described above with respect to FIG. 10, the characteristic of the pump motor can be force velocity 702. In another embodiment, the characteristic of the pump motor can be force acceleration 704. In other embodiments, other characteristics of the pump motor can be utilized, such as linear rate of plunger travel.

At 806, the infusion pump motor is driven at a second rate. In embodiments, the second rate can be a slower rate than the first rate, or a transitional rate different than the first rate.

Optionally, at 808, the infusion pump motor can be driven at a third rate. In an embodiment, the third rate is a steady state rate at which programmed delivery is desired. In embodiments (not shown in FIG. 11), the driving of the pump motor at a third rate 808 can be preceded by a determination of an inflection point or other value of a characteristic of the pump motor. In embodiments, the characteristic of the pump motor can be the same characteristic as evaluated at 804. In other embodiments, the characteristic of the pump motor can be a different characteristic than was evaluated at 804.

Figure 12A:
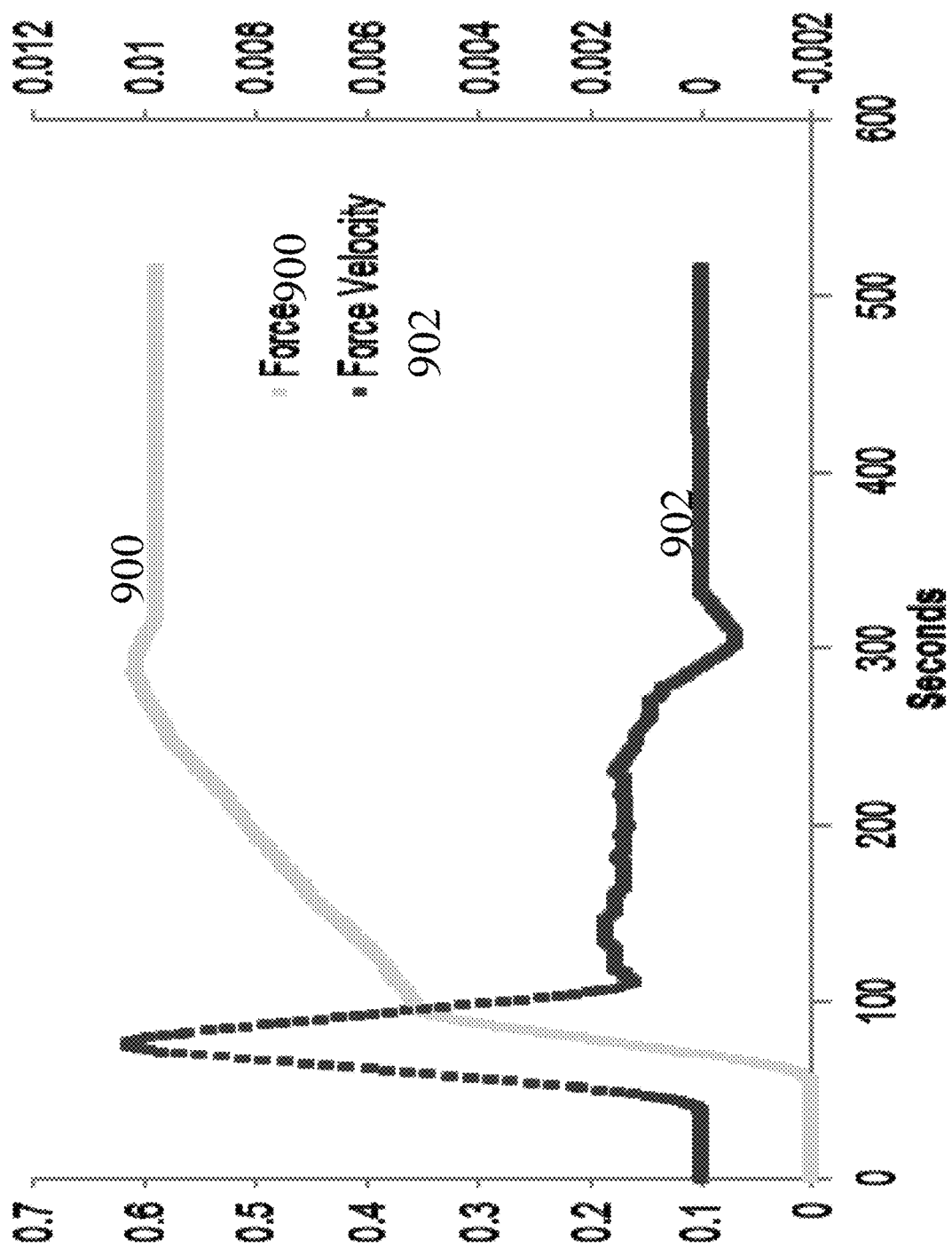
FIGS. 12A and 12B are graphs of force, force velocity, and force acceleration with respect to time, illustrating a minimized startup time according to the startup algorithm of FIG. 11, according to embodiments.
Figure 12B:
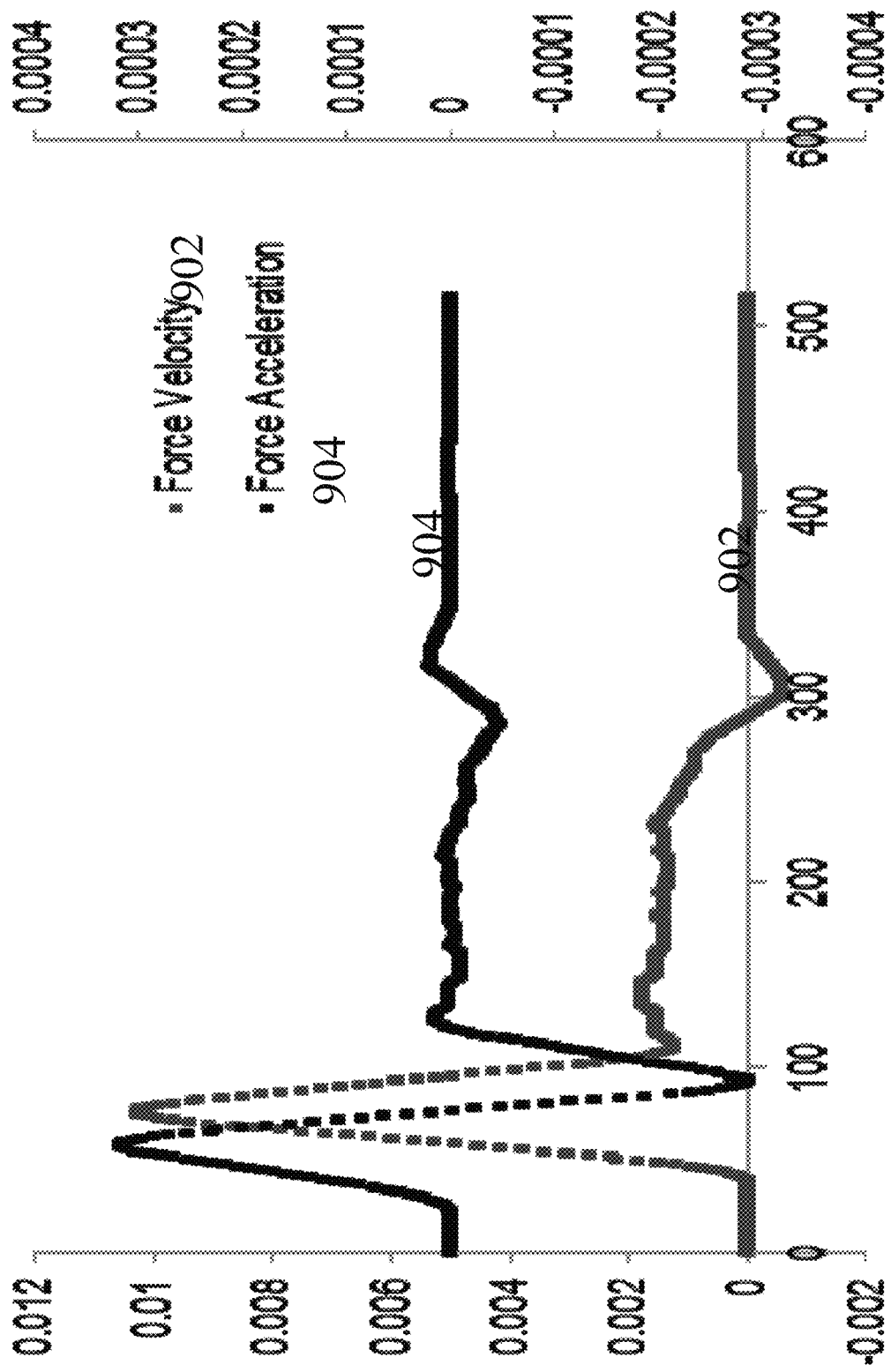

Referring to FIGS. 12A and 12B, graphs illustrating the results of implementation of a startup algorithm—for example, startup algorithm 800—are shown. The data graphed illustrates the transition from 20 mL/hr to 1 mL/hr when a force acceleration inflection point is selected as the transitional motor control point. As illustrated, there is minimal overshoot or overdelivery, and the pump reaches steady state at 300 seconds.

Figure 13:
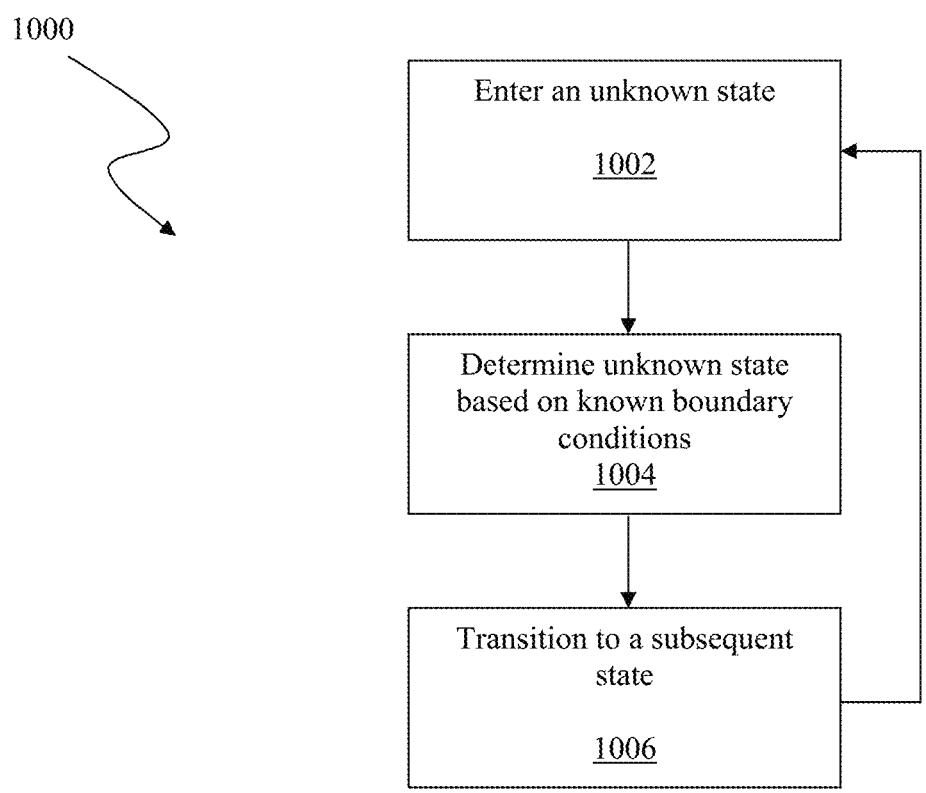
FIG. 13 is a flowchart of a state identification startup algorithm, according to an embodiment.

Referring to FIG. 13, and again to FIG. 9, a flowchart of an embodiment of a state identification startup algorithm 1000 is illustrated. Embodiments of startup algorithm 1000 can be implemented by, for example, and referring to FIG. 3, pumping mechanism 108 as directed by, for example, pump control subsystem 106 and startup module 116.

State identification startup algorithm 1000 can be utilized in complex or untested startup sequences. Embodiments of algorithm 1000 provide safety boundaries around startup sequences. For example, algorithm 1000 provides a wrapper around given startup commands by determining respective states based on known boundary conditions.

For example, at 1002, an unknown state is entered. The state can be unknown due to, as mentioned, a complex or untested startup sequence being implemented. In embodiments, the state can be unknown because of a software or hardware error which effectively "drops" the algorithm at a point in which it is unknown how far the startup sequence has progressed. In other words, the algorithm has no record or data as to what steps the algorithm has already executed. For example, it would be impossible to know, based merely on time, whether the startup sequence was in State 1, State 7, or any state in between States 1 and 7. It could therefore be problematic or perhaps even dangerous to drive the motor faster, slower, (or even at the same rate, in certain cases) without first understanding the point at which the startup sequence currently exists.

At 1004, the unknown state is determined based on known boundary conditions. The boundary conditions can be determined by, for example, determination of inflection points as illustrated in FIGS. 10-11 and/or as described with respect to FIG. 9 and Table 1.

At 1006, algorithm 1000 allows the startup sequence to transition to a subsequent state. If, as depicted, the subsequent state is also unknown, algorithm 1000 proceeds recursively back to 1002. The subsequent unknown state can then be determined at 1004 based on that state's boundary conditions. In other embodiments, future states can be generally known and characterized. In such embodiments, algorithm 1000 can proceed to a known state. Embodiments of the methods disclosed herein therefore enable the software implemented by startup module 116 to more safely transition motor control.

Figure 14:
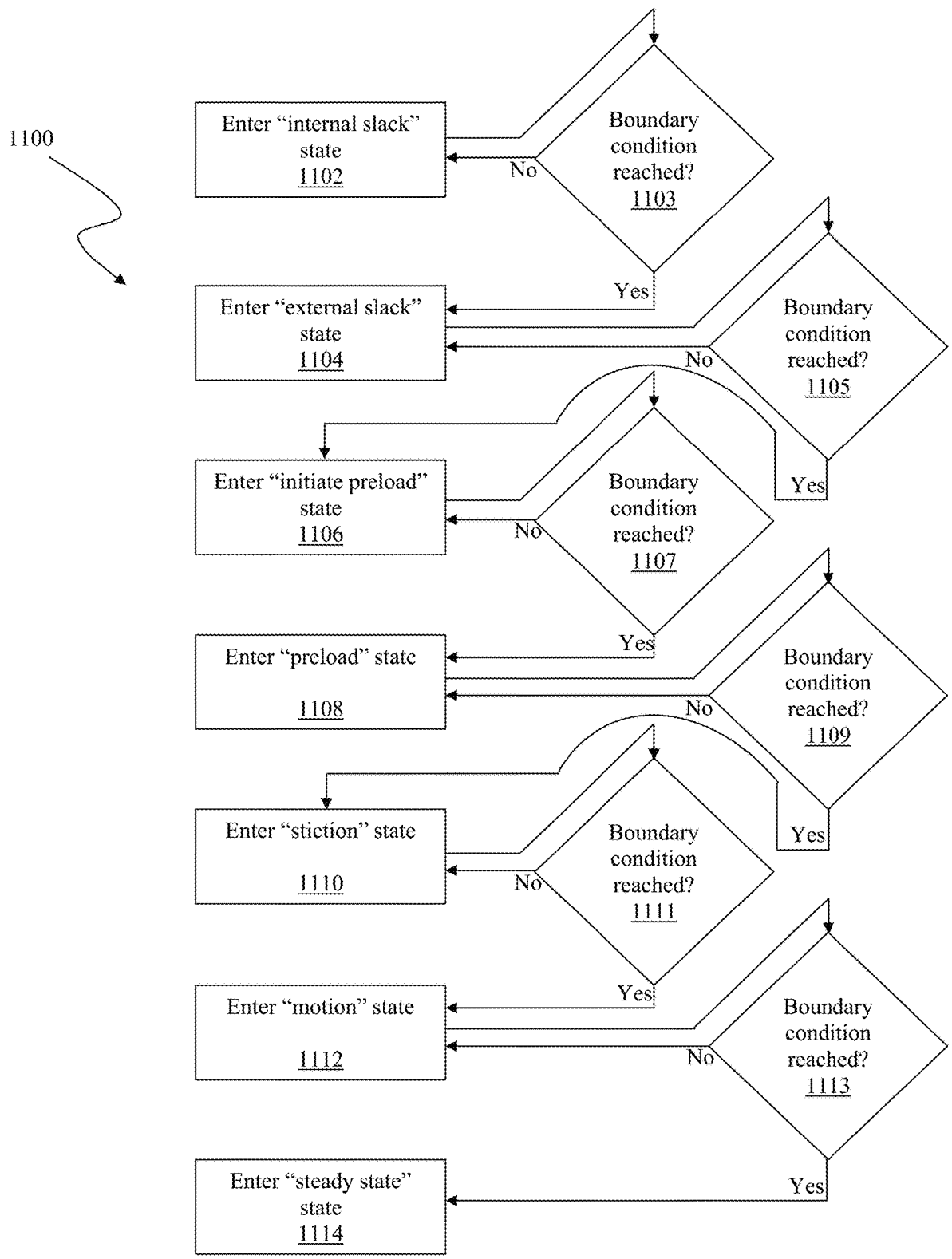
FIG. 14 is a flowchart of a state identification startup algorithm, according to an embodiment.

Referring to FIG. 14, and again to FIG. 9, a flowchart of an embodiment of a state identification startup algorithm 1100 is illustrated. Embodiments of startup algorithm 1100 can be implemented by, for example, and referring to FIG. 3, pumping mechanism 108 as directed by, for example, pump control subsystem 106 and startup module 116.

Startup algorithm 1100 begins by entering internal slack state 1102. Startup algorithm 1100 remains in internal slack state 1102 until one or more boundary conditions 1103 are reached. If the one or more boundary conditions are reached 1103, startup algorithm 1100 exits internal slack state 1102 and enters external slack state 1104.

Startup algorithm 1100 remains in external slack state 1104 until one or more boundary conditions 1105 are reached. If the one or more boundary conditions are reached 1105, startup algorithm 1100 exits external slack state 1104 and enters initiate preload state 1106.

Startup algorithm 1100 remains in initiate preload state 1106 until one or more boundary conditions 1107 are reached. If the one or more boundary conditions are reached 1107, startup algorithm 1100 exits initiate preload state 1106 and enters preload state 1108.

Startup algorithm 1100 remains in preload state 1108 until one or more boundary conditions 1109 are reached. If the one or more boundary conditions are reached 1109, startup algorithm 1100 exits preload state 1108 and enters stiction state 1110.

Startup algorithm 1100 remains in stiction state 1110 until one or more boundary conditions 1111 are reached. If the one or more boundary conditions are reached 1111, startup algorithm 1100 exits stiction state 1110 and enters motion state 1112.

Startup algorithm 1100 remains in motion state 1112 until one or more boundary conditions 1113 are reached. If the one or more boundary conditions are reached 1113, startup algorithm 1100 exits motion state 1112 and enters steady state 1114.

Boundary conditions 1103, 1105, 1107, 1109, 1111, and 1113 can be determined by, for example, determination of inflection points as illustrated in FIGS. 10-11 and/or as described with respect to FIG. 9 and Table 1.

PID-F Startup Algorithm

In an embodiment, a pump startup algorithm can be implemented by a PID-F algorithm and control circuit. The term "PID-F" refers to a control circuit that includes: a "Proportional" component, relating to a stable mechanical system wherein inputs equal output; an "Integrator" component, relating to error; a "Derivative" component, relating to rate changes; and a "Feed-forward" component, relating to predictable, repeatable, and short time duration events.

Figure 15:
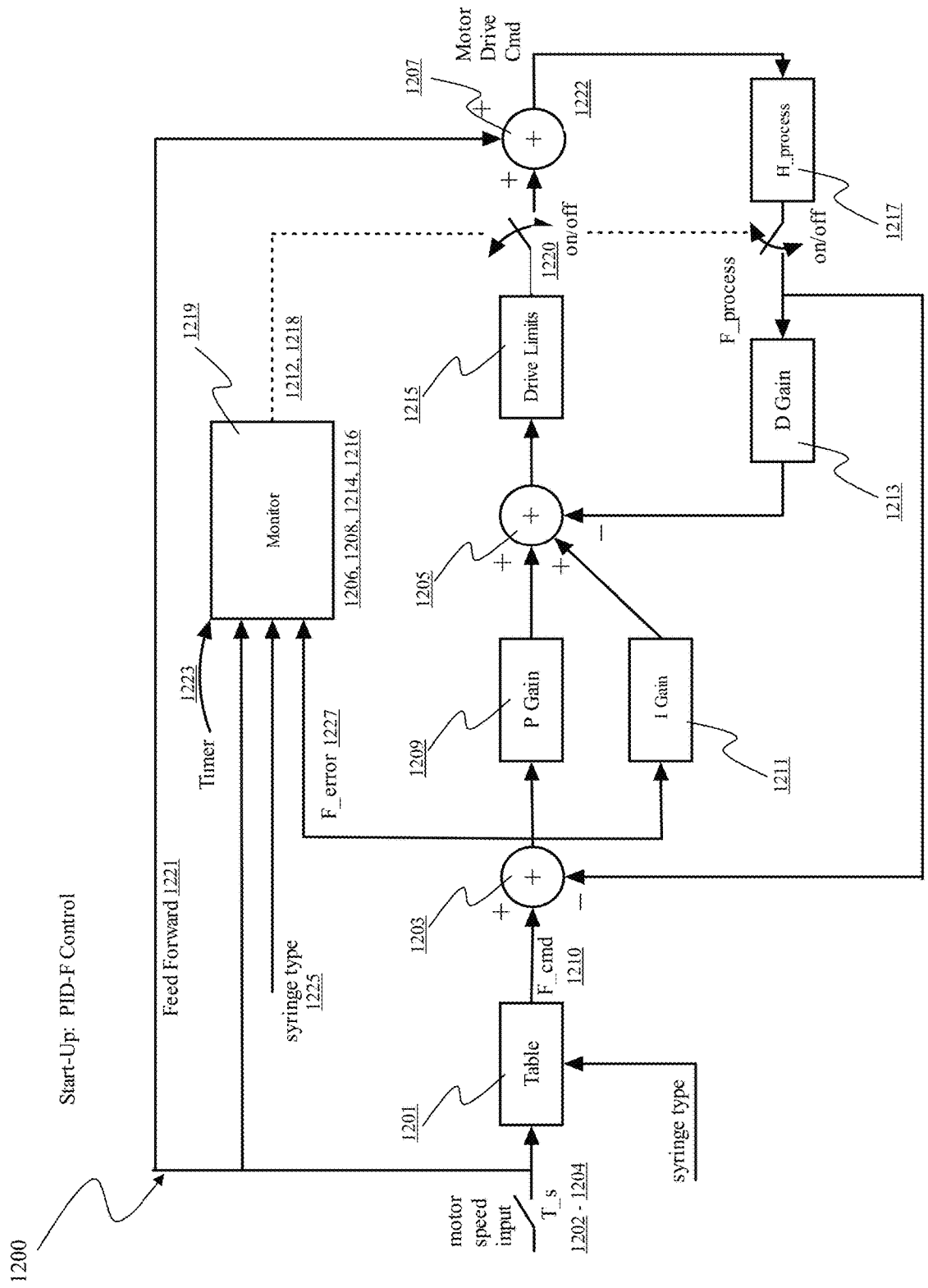
FIG. 15 is a schematic diagram of a control circuit for a startup algorithm, according to an embodiment.

Referring to FIG. 15, a schematic diagram of a PID-F control circuit 1200 for a startup algorithm is depicted. Control circuit 1200 comprises a control loop feedback controller. In general, control circuit 1200 calculates an "error" value as a difference between a measured process variable and a desired setpoint. Control circuit 1200 minimizes this error by adjusting the process control inputs. Generally, control circuit 1200 can initially drive the motor at a high rate, and then reduce the motor drive rate based on the control loop feedback controller. Effectively, then, control circuit 1200 functions to selectively reduce the motor drive rate.

The control circuit can be implemented, for example, on pump 102, and particularly, processor 112 and/or memory 114. One skilled in the art will appreciate that startup module 116 can also include components of the control circuit and related processing. In an embodiment, the control output comprises two commands. The first command is a user motor drive rate command, in a feed-forward (the "F", in "PID-F") path 1221 as will be described. The second command is a PID-based closed-loop force control. In embodiments, a trigger switch point for varying the motor control drive rate is based on closed-loop error.

According to an embodiment, an input to control circuit 1200 comprises motor speed, or the user-commanded pump rate. In embodiments, syringe type is another input, which is utilized by a lookup table 1201, as will be described. In another embodiment a timer 1223 input is a so-called "watchdog" which limits an amount of time in performing the control, and stops the processing if the time is exceeded. According to an embodiment, motor speed is output by output control circuit 1200. In embodiments, the motor speed output is the motor speed to run at a particular delivery rate.

In an embodiment, table 1201 comprises a look-up table. In an embodiment, motor speed and syringe type are input to table 1201. Other inputs are, of course, possible according to embodiments of subject matter hereof. Table 1201 can output a force command, F_cmd 1210 to the PID closed loop control. In an embodiment, F_cmd 1210 is a function of motor speed and syringe type.

First summer 1203 generates an error signal. In an embodiment, the error is calculated by: Error=F_cmd−F_process. As will be described, F_process is the output from H_process 1217.

P Gain 1209 comprises the proportional gain. The error output from first summer 1203, F_error, is input to P Gain 1209. In an embodiment, the function of P Gain 1209 is: P_out=P_gain*F_error.

I Gain 1211 comprises the integral gain. In an embodiment, I Gain 1211 stores a running sum of the error times the I gain. Typical use is to drive the control to match the commanded input, making F_error=0. In an embodiment, the output of I Gain 1211 is calculated by: I_out=(I_gain*F_error)*sample period+I_out_last; I_out_last=I_out.

D Gain 1213 comprises the derivative gain. In an embodiment, the processing of D Gain 1213 is: D_out=(F_error−F_error_last)/sample period.

Second summer 1205 combines the P Gain 1209, I Gain 1211, and D Gain 1213 outputs. In an embodiment, the output provided by Second summer 1205 is calculated by: Second summer 1205 Output=P Gain out+I Gain out−D Gain out.

Drive Limits 1215 limits the PID contribution output contribution. It provides an upper level so-called "clamping" effect, in embodiments.

Third summer 1207 combines the Drive Limits 1215 signal and the feed-forward signal and outputs to the motor drive 1222 according to: Output=motor speed input+PID_out. The feed-forward signal therefore provides the motor speed as input to third summer 1207 of control circuit 1200.

On/off switch 1220 functions to, alternatively, include or block out the closed-loop PID of P Gain 1209, I Gain 1211, and D Gain 1213. When blocked out, feed-forward is the only signal going to the motor.

H_process 1217 comprises the pump dynamics. According to an embodiment, H_process 1217 receives motor drive 1222 as an input, and outputs the force sensor data (F_Process).

In an embodiment, monitor 1219 comprises the control algorithm(s). In an embodiment, monitor 1219 monitors the control conditions and determines when to block out the PID via on/off switch 1220. In embodiments, for example, as shown in FIG. 15, timer 1223, syringe type 1225, and F_error 1227 can be input to monitor 1219 to determine the switch 1220 conditions. In another embodiment, only timer 1223 is input to monitor 1219. In an embodiment, timer 1223 is a watchdog limiting the amount of time performing the control algorithm, stopping the algorithm if the time limit is exceeded. In another embodiment, only syringe type 1225 is input to monitor 1219. In embodiments, one or more measures of syringe type 1225 or syringe distance (not shown) can be input to monitor 1219. In another embodiment, only F_error 1227 is input to monitor 1219 to determine the switch 1220 conditions. In other embodiments, combinations or the aforementioned inputs or other inputs can be utilized by monitor 1219.

Figure 16:
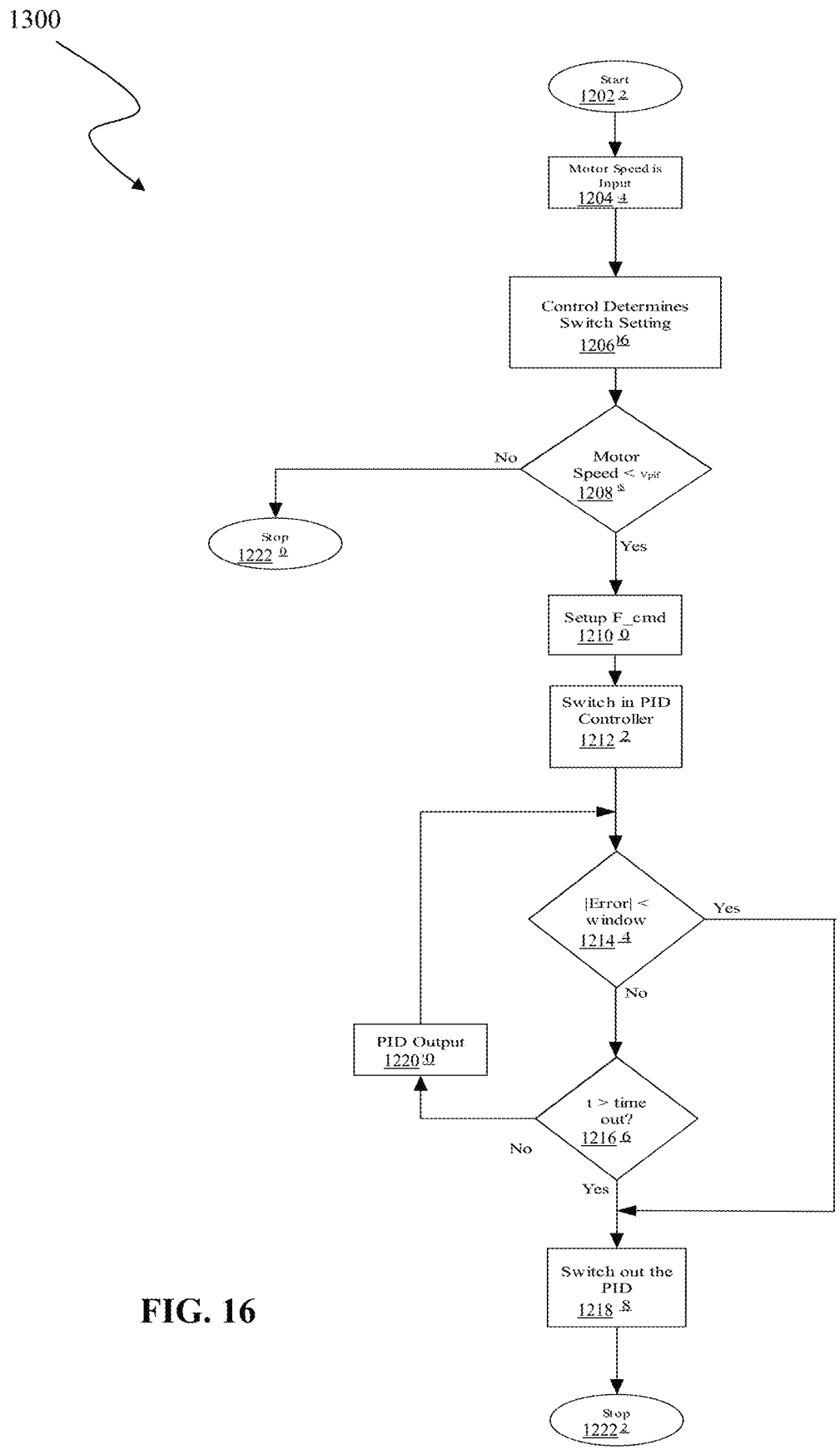
FIG. 16 is a flowchart of operation for a startup algorithm implementing the control circuit of FIG. 15.

Referring also to FIG. 16, a flowchart of operation for a startup algorithm 1300 implementing the PID-F control 1200 of FIG. 15 is depicted. The element labels of control 1200 are reflected in FIG. 16 for ease of relation between the two figures.

Startup algorithm 1300 begins at start 1202. At 1204, motor speed is input to control circuit 1200. At 1206, the control determines switch setting. At 1208, if the motor speed is equal to or greater than a given value, for example, $V_{pip}$, or the minimum motor rate for normal startup, below which the start algorithm becomes active, startup algorithm 1300 proceeds to stop 1222 (because in such a condition, the startup algorithm is not needed to quickly start the pump). But if, at 1208, the motor speed is less than a given value (in embodiments, $V_{pif}$), F_cmd is set at 1210 (because in such a condition, the startup algorithm is needed to quickly start the pump). As described, F_cmd 1210 can be set by lookup table value according to inputs of motor speed and syringe type.

At 1212, PID on/off 1220 is switched according to output from monitor 1219. At 1214, the absolute value of the error calculated is checked against a window. If the absolute value of the error calculated is equal to or greater than the window, a time duration t is checked against a timeout. If the time duration t is less than or equal to the timeout, startup algorithm 1300 recursively proceeds to PID output 1220 and subsequently, back to 1214, the determination of the absolute value of the error against a window. If the time duration t is greater than the timeout, startup algorithm 1300 proceeds to switch out (or block out) the PID at 1218. If, referring again to 1214, the absolute value of the error calculated is less than the window, startup algorithm 1300 proceeds to switch out (or block out) the PID at 1218. Startup algorithm 1300 ends at stop 1222.

Embodiments of PID-F startup algorithm 1300 can be implemented by, for example, and referring to FIG. 3, pumping mechanism 108 as directed by, for example, pump control subsystem 106 and startup module 116.

Combination Startup Algorithms

In embodiments, a pump startup algorithm can incorporate aspects of the Motor Rate Startup Algorithm, the State Identification Startup Algorithm, and/or the PID-F Startup Algorithm in combination. For example, a monitor of the embodiment of a PID-F Startup Algorithm can determine the current position along the startup sequence, such as any one of the seven states illustrated in FIG. 9 of embodiments of a State Identification Startup Algorithm. In embodiments, then, pump systems include combinations of software and hardware to reach targeted delivery rate or steady state in minimal time. One skilled in the art will readily appreciate that startup algorithms according to the subject matter disclosed herein can stop or decrease the rate of pump motor or plunger motion at any of the state condition boundaries or within any of the state conditions, segments, or phases identified by, for example, the Motor Rate Startup Algorithm, the State Identification Startup Algorithm, and/or the PID-F Startup Algorithm, alone or in combination.

Characterization of Breakout Forces

In embodiments, startup algorithms can utilize a database of characterized syringe breakout forces as aforementioned. For example, referring to FIG. 3, network/PC 104 can provide, via I/O port 110, access for pump 102 to a database of breakout forces. In embodiments, memory 114 can also store data for breakout forces.

As described above, each pump has unique gearing, clutch assemblies, linkage couplings, and manufacturing or assembly tolerances that all introduce varying amounts of discontinuity that in turn inhibit or prevent motive force from being instantly or completely translated into fluid flow. By determination of a particular syringe and its particular breakout force, determination of the individual startup states and their respective progression can be further defined and characterized. As a result, startup sequence progression can be more easily transitioned. In embodiments, the particular breakout forces are stored by, for example, table 1201. In embodiments, table 1201 can comprise not just a single table, but a plurality of tables. In embodiments, table 1201 can comprise parameters or data that affect pump startup reaching steady state. Other parameters that can be stored in, for example, table 1201 or a plurality of tables, are the age of the pump (new pump, old pump, hours of use, etc.), a sensor calibration, tubing type (material, friction coefficient, etc.), tubing diameter, tubing length, needle size, and the viscosity of the infusing substance, among others. One skilled in the art will readily appreciate that any modifying parameter can be utilized in table 1201.

Various embodiments of systems, devices, and methods have been described herein. These embodiments are given only by way of example and are not intended to limit the scope of subject matter hereof. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized commensurate with the scope of subject matter hereof.

Persons of ordinary skill in the relevant arts will recognize that subject matter hereof may comprise fewer features than illustrated in any individual embodiment described above. The embodiments described herein are not meant to be an exhaustive presentation of the ways in which the various features of subject matter hereof may be combined. Accordingly, the embodiments are not mutually exclusive combinations of features; rather, the subject matter hereof may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims of subject matter hereof, it is expressly intended that the provisions of Section 112, sixth paragraph of 35 U.S.C. are not to be invoked unless the specific terms "means for" or "step for" are recited in a claim.

The invention claimed is:

1. A method of driving an infusion pump motor of an infusion pump configured to reach a steady state, target delivery rate with minimal delay, the method comprising:
   driving the infusion pump motor at a first rate;
   sensing a force generated by driving the infusion pump motor;
   determining an inflection point of a sensed parameter; and
   upon determining when the inflection point is reached, driving the infusion pump motor at a second, gradual, decreasing transitional rate, the transitional rate being an inverse function of the force sensed.

2. The method of driving an infusion pump motor of claim 1, wherein the sensed parameter is an infusion pump motor plunger driver force.

3. The method of driving an infusion pump motor of claim 1, wherein determining an inflection point further comprises deriving at least one parameter.

4. The method of driving an infusion pump motor of claim 3, wherein the derived parameter is at least one of force velocity or force acceleration.

5. The method of driving an infusion pump motor of claim 3, wherein the first rate is greater than the second rate and the second rate is greater than the third rate.

6. The method of driving an infusion pump motor of claim 1, further comprising driving the infusion pump motor at a third rate.

7. The method of driving an infusion pump motor of claim 1, wherein the first rate is greater than the second rate.

8. The method of driving an infusion pump motor of claim 7, wherein the second rate is stepped or curved.

9. The method of driving an infusion pump motor of claim 1, further comprising characterizing a breakout force.

\* \* \* \* \*

UNITED STATES PATENT AND TRADEMARK OFFICE
CERTIFICATE OF CORRECTION

| | | |
|---|---|---|
| PATENT NO. | : 11,179,515 B2 | Page 1 of 1 |
| APPLICATION NO. | : 16/388388 | |
| DATED | : November 23, 2021 | |
| INVENTOR(S) | : Adams et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 221 days.

Signed and Sealed this
Fourteenth Day of February, 2023

Katherine Kelly Vidal
*Director of the United States Patent and Trademark Office*